(12) United States Patent
Kliman et al.

(10) Patent No.: US 6,733,962 B2
(45) Date of Patent: May 11, 2004

(54) METHODS OF DIAGNOSING AND MONITORING ENDOMETRIAL GLANDULAR DEVELOPMENT

(75) Inventors: Harvey J. Kliman, 161 Ford Rd., New Haven, CT (US) 06525; Rebecca L. Dubowy, Chicago, IL (US)

(73) Assignee: Harvey J. Kliman, New Haven, CT (US)

( * ) Notice: Subject to any disclaimer, the term of this patent is extended or adjusted under 35 U.S.C. 154(b) by 28 days.

(21) Appl. No.: 09/801,470

(22) Filed: Mar. 8, 2001

(65) Prior Publication Data

US 2002/0006628 A1 Jan. 17, 2002

Related U.S. Application Data

(60) Provisional application No. 60/187,682, filed on Mar. 8, 2000.

(51) Int. Cl.[7] .................................................. C12Q 1/00

(52) U.S. Cl. ........................................... 435/4; 435/7.1

(58) Field of Search ..................... 435/4, 7.1

(56) References Cited

U.S. PATENT DOCUMENTS

| | | | |
|---|---|---|---|
| 5,599,680 A | 2/1997 | Feinberg et al. | 435/7.21 |
| 6,165,753 A | 12/2000 | Coats et al. | 435/69.1 |

OTHER PUBLICATIONS

Anderson, T. et al., "Stage specific alterations in the apical membrane glycoproteins on endometrial epithelial cells related to implantation in rabbits", *Biol. Reprod.,* 1986, 34:701–720.
Bamberger, A–M. et al., "Strongly reduced expression of the cell cycle inhibitor p27 in endometrial neoplasia", *Virchows Arch.,* 1999, 434:423–28.
Beresford, S. et al., "Risk of endometrial cancer in relation to use of oestrogen combined with cyclic progestagen therapy in postmenopausal women", *The Lancet,* 1997, 349:458–461.
Bergh, P., "The impact of embryonic development and endometrial maturity on the timing of implantation", *Fertil Steril.,* 1992, 58(3):537–542.
Blasco, L., "Dyssynchrony in the maturation of endometrial glands and stroma", *Fertil. Steril.,* 1994, 61(4):596–7.
Burger, C. et al., "Hormone replacement therapy in women treated for gynaecological malignancy", *Maturitas,* 1999, 32:69–76.
Bush, T., "Evidence for primary and secondary prevention of coronary artery disease in women taking oestrogen replacement therapy", *Eur. Heart J.,* 1996, 17(Supplement D):9–14.
Castelbaum, A., "Timing of the endometrial biopsy may be critical for the accurate diagnosis of luteal phase deficiency", *Fertil Steril.,* 61(3):443–447.

Castellsague J., "Recent epidemiological studies of the association between hormone replacement therapy and venous thromboembolism", *Drug Safety,* 1998, 18(2):117–23.
Collaborative Group on Hormonal Factors in Breast Cancer. "Breast cancer and hormone replacement therapy: collaborative reanalysis of data from 51 epidemiological studies of 52 705 women with breast cancer and 108 411 women without breast cancer", *The Lancet,* 1997, 350:1047–1059.
Creus, M. et al., "Integrin expression in Normal and out–of–phase endometria", *Hum. Reprod.,* 1998, 13(12):3460–3468.
Design of the women's health initiative clinical trial and observational study, The women's health initiative study group, *Control Clin Trials,* 1998, 19:61–109.
Dockery, P. et al., "Changes in nuclear morphology in the human endometrial glandular epithelium in women with unexplained infertility", *Hum Reprod,* 1996, 11(10):2251–2256.
Enders, A. et al., "Surface coats of the mouse blastocyst and the uterus during the preimplantation period", *Anat. Rec.,* 1974, 180:31–46.
Giangrande, P. et al., "The opposing transcriptional activities of the two isoforms of the human progesterone receptor are due to differential cofactor binding", *Mol. Cell Biol.,* 2000, 20(9):3102–3115.
Gibson, M., et al., "Error in histologic dating of secretory endometrium: variance component analysis", *Fertil Steril.,* 1991, 56(2):242–247.
Grodstein, F. et al., "Postmenopausal hormone therapy and mortality", N Engl J Med, 1997, 336(25):1769–1775.
Gurpide, E. et al., "Introduction: research on the human endometrium", *Ann New York Acad Sci.,* 1990, 622:1–5.
Hamel, P. et al., "G1 cyclins and control of the cell division cycle in normal and transformed cells", *Cancer Investigation,* 1997, 15(2):143–152.
Hendrickson, M. et al., "Surgical pathology of the uterine corpus", *Major Problems Pathology,* 1980, 12:36–98.

(List continued on next page.)

Primary Examiner—Patrick J. Nolan
(74) Attorney, Agent, or Firm—Cozen O'Connor, P.C.

(57) ABSTRACT

Methods of diagnosing an abnormality in endometrial glandular development in a woman suspected of being infertile are disclosed. Methods of predicting abnormal endometrial glandular development are also disclosed. In addition, methods of assessing the suitability of the endometrium for embryo implantation in a woman undergoing ovulation induction are disclosed. Further, methods of evaluating the effect of a hormonal protocol on endometrial glandular development in a woman undergoing a hormonal protocol to produce a mock cycle are disclosed. Methods of evaluating a hormone replacement therapy protocol in a woman undergoing hormone replacement therapy are disclosed. Further, methods of diagnosing endometrial glandular mitotic arrest in a woman suspected of having endometrial hyperplasia are disclosed.

74 Claims, 4 Drawing Sheets

OTHER PUBLICATIONS

Hewitt, K. et al., "Disappearance of anionic sites from the surface of the rat endometrial epithelium at the time of blastocyst implantation", *Biol Reprod*, 1979, 21:691–707.

Johannisson, E. et al., "Endometrial morphology and peripheral hormone levels in women with regular menstural cycles", *Fertil Steril.*, 1987, 48(3):401–408.

Johannisson, E. et al., "Morphometric analysis of the human endometrium in relation to peripheral hormone levels", *Fertil Steril., 1982*, 38(5):564–571.

Kakar, F. et al., "Non–contraceptive estrogen use and risk of gallstone disease in women", *Am J Public Health*, 1988, 78(5):564–566.

Keller, C. et al., "Supplemental and complementary alternatives to hormone replacement therapy", *J of Amer Acad Nurse Pract.*, 1999, 11(5):187–198.

Kliman H. et al., "MAG mucin expression abnormalities in natural cycle biopsies predict subsequent IVF failure", Society for Reproductive Medicine, 1997, Cincinnati (Abstr.).

Kliman, H. et al., "Absence of biochemical or morphologic markers of endometrial glandular development in a mock cycle predicts pregnancy failure in a subsequent donor oocyte transfer cycle", American Society for Reproductive Medicine, 1998, San Francisco. (Abstr.).

Kliman, H. et al., "A mucin–like glycoprotein identified by MAG (mouse ascites golgi) antibodies", *A J Pathol*, 1995, 146(1):166–181.

Kumar, N. et al., "Selective down–regulation of progesterone receptor isoform B in poorly differentiated human endometrial cancer cells: Implications for unopposed estrogen action", *Cancer Research*, 1998, 58:1860–1865.

Kurman, R. et al., "Endometrial hyperplasia and related cellular changes" in Blausteins's pathology of the female genital tract, Ed: Kurman RJ. Springer–Verlag, New York, pp. 411–437.

Kwon, T. et al., "Overexpression of cyclin E and cyclin–Dependent kinase inhibitors (p27 Kip1): Effect on cell cycle regulation in HeLa cells", *Biochm and Biophys Research Comm.*, 1997, 238:534–538.

Leslie, K. et al., "Differential expression of the A and B isoforms of progesterone receptor in human endometiral cancer cells", *Ann New York Acad. Sci.*, 1997, 828:17–26

Lessey, B. et al., "Integrins as markers of uterine receptivity in women with primary unexplained infertility", *Fertil Steril.*, 1995, 63(3):535–542.

Lessey, B. et al., "Aberrant integrin expression in the endometrium of women with endometriosis", *J Clin Endocrinol Metab.*, 1994, 79(2):643–649.

Lessey, B. et al., "Integrin adhesion molecules in the human endometrium. Correlation with the normal and abnormal menstural cycle", *J Clin Invest.*, 1992, 90:188–195.

Li, T–C. et al., "A quantitative study of endometrial development in the luteal phase: comparison between women with unexplained infertility and normal fertility", *Brit J Ob Gyn.*, 1990, 97:576–582.

Li, T–C. et al., "How precise is histologic dating of endometrium using the standard dating criteria?", *Fertil Steril.*, 1989, 51(5):759–763.

Li, T–C. et al., "A new method of histologic dating of human endometrium in the luteal phase", *Fertil Steril.*, 1988, 50(1):52–60.

Lloyd, R. et al., "p27$^{kip1}$: A multifunctional cyclin–dependent kinase inhibitor with prognositc significance in human cancers", *Am J Pathol.*, 1999, 154(2):313–323.

Meyer, W. et al., "Hydrosalpinges adversely affect markers of endometrial receptivity", *Human Reproduction*, 1997, 12(7):1393–1398.

Mishell, D.R., Davajan, V., and Lobo, R.A.,1991, Infertility, contraception and reproductive endocrinology, Blackwell Scientific Publications.

Morgan, D. et al., "Cyclin–dependent kinases: engines, clocks, and microprocessors", *Annu Rev Cell Dev. Biol.*, 1997, 13:261–291.

Mosher, W., "Infertility: why business is booming", *Am Demograph*, 1987, 9:42–43.

Mote, P. et al., "Colocalization of progesterone receptors A and B by dual immunofluorescnet histochemistry in human endometrium during the menstrual cycle", *J. Clin. Endocrinol. Metab.*, 1999, 84(8):2963–2971.

Musgrove, E. et al., "Cell cycle control by steroid hormones", *Sem Cancer Biol.*, 1994, 5:381–389.

Musgrove, E. et al., "Mechanisms of cyclin–dependent kinase inactivation by progestins", *Mol Cell Biol*, 1998, 18(4):1812–1825.

Navot, D. et al., "The window of embryo transfer and the efficienty of human conception in vitro", *Fertil Steril.*, 1991, 55(1):114–118.

Noyes, R., "Uniformity of secretory endometrium: study of multiple sections from 100 uteri removed at operation", *Fertil Steril.*, 1956, 7:103–109.

Noyes, R. et al., "Accuracy of endometrial dating", *Fertil Steril.*, 1953, 4(6):504–517.

Noyes, R. et al., "Dating the endometrial biopsy", *Fertil Steril.*, 1950, 1(1):3–25.

Orend, G., "Cytoplasmic displacement of cyclin E–CDK2 inhibitors p21Cip1 and p27Kip1 in anchorage– independent cells", *Oncogene*, 1998, 16:2575–2583.

Ovulation Drugs, A Guide for Patients. American Society for Reproductive Medicine, 2000, 1209 Montgomery Highway, Birmingham AL 35216–9822.

Pedersen T., "Statin trials and goals of cholesterol–lowering therapy after AMI", *Am Heart J*, 1999; 138 (2 Pt 2):177–82.

Pike, M. et al., "Estrogen–progestin replacement therapy and endometrial cancer", *J Natl Cancer Inst*, 1997, 89(15):1110–1116.

Reid, I., "Pharmacological management of osteoporosis in postmenopausal women: a comparative review", *Drugs Aging*, 1999;15(5):349–363.

Reynisdóttir, I. et al., "The subcellular locations of p15$^{ink4b}$ and p27$^{Kip1}$ coordinated their inhibitory interactions with CDK4 and CDK2", *Genes Dev.*, 1997, 11:492–503.

Rosano, G. et al., "Cardiovascular pharmacology of hormone replacement therapy", *Drugs Aging*, 1999, 15(3):219–234.

Rozenberg, S. et al., "Osteoporosis Managment,", *Int J Fertil Womens Med*, 1999, 44(5):241–249.

Ross, R. et al., "Effect of hormone replacement therapy on breast cancer risk: estrogen versus estrogen plus progestin", *J Natl Cancer Inst.*, 2000, 92(4):328–332.

Rossouw, J., "Hormone replacment therapy and cardiovascular disease", *Curr Opin Lipidol.*, 1999, 10:429–434.

Satyaswaroop, P. et al., "Isolation and culture of human endometrial glands", *J Clin Endocrinol Metab.*, 1979, 48(4):639–641.

Schairer, C. et al., "Menopausal estrogen and estrogen–progestin replacement therapy and breast cancer risk", *JAMA*, 2000, 283(4):485–491.

Scharbo–Dehaan, M., "Hormone replacement therapy", *Nurse Pract.* 1996, 21(12 Pt 2):1–13.

Schatz, F. et al., "Studies on human endometrial cells in primary culture", *Ann New York Acad Sci.,* 1991, 622:80–88.

Schneider, D. et al., "Timing of postmenopausal estrogen for optimal bone mineral density: the Rancho Bernardo Study", *JAMA,* 1997, 277(7):543–547.

Scott, R. et al., "The effect of interobserver variation in dating endometrial histology on the diagnosis of luteal phase defects", *Fertil Steril.,* 1988, 50(6): 888–892.

Seifert, M. et al., "Estrogen replacement therapy in women with a history of breast cancer", *Maturitas,* 1999, 32:63–68.

Sheaff, R. et al., "Cyclin E–CDK2 is a regulator of $p27^{Kip1}$", *Genes Devel.,* 1997, 11:1464–1478.

Shiozawa, T. et al., "Relationship between the expression of cyclins/cyclin–dependent kinases and sex– steroid receptors/Ki67 in normal human endometrial glands and stroma during the menstrual cycle", *Mol Hum Reprod.,* 2(10):745–752.

Shiozawa, T. et al., "Involement of cyclin–dependent kinase inhibitor $p27^{Kip1}$ in growth inhibition of endometrium in the secretory phase and of hyperplastic endometrium treated with progesterone", *Mol Hum Reprod.,* 4(9):899–905.

Singh, S. et al., "Loss or altered subcellular localization of p27 in Barrett's associated adenocarcinoma", *Cancer Res.,* 1998, 58:1730–1735.

Smith, S. et al., "Endometrial biopsy dating: interobserver variation and its impact on clinical practice", *J Repro Med.,* 1995, 40(1):1–3.

Society for assisted reproductive technology 1997 national report, 1999, Centers for Disease Control, Atlanta, GA (The report can be accessed at the Centers for Disease Control's web site which is the direct cite to the PDF file).

Soucek, T. et al., "Inactivation of the cyclin–dependent kinase inhibitor p27 upon loss of the tuberous sclerosis complex gene–2", *Proc Natl Acad Sci. USA,* 1998, 95:15653–15658.

Tang, M–X. et al., "Effect of oestrogen during menopause on risk and age at onset of Alzheimer's disease", *The Lancet,* 1996, 348(9025):429–432.

Tavani, A. et al., "The adverse effects of hormone replacement therapy", *Drugs Aging,* 1999, 14(5):347–357.

Taylor, H. et al., "HOXA10 is expressed in response to sex steroids at the time of implantation in the human endometrium", *J Clin Invest.,* 1998, 101(7):1379–1384.

Third Party Reproduction, A Guide for Patients. American Society for Reproductive Medicine. 1996. 1209 Motgomery Highway, Birmingham AL 35216–9822.

Treloar, A. et al., "Variation of the human menstrual cycle through reproductive life", *Internat J Fertil.,* 1967, 12(1, pt. 2):77–126.

Vassilopoulou–Sellin et al., "Estrogen replacement therapy after localized breast cancer: clinical outcome of 319 women followed prospectively", *J Clin Oncol,* 1999, 17(5):1482–1487.

Vassilopoulou–Sellin et al., "Randomized prospective trial of estrogen–replacement therapy in women with a history of breast cancer", *J of Natl Cancer Inst Monog.,* 1994, 16:153–159.

Wang, H. et al., "Progesterone receptor subtype B is differentially regulated in human endometrial stroma", *Mol. Hum. Reprod.,* 1998, 4(4):407–412.

Yen, S.S.C., Jaffe, R.B., and Barbieri, R.L., 1999, Reproductive endocrinology: physiology, pathophysiology, and clinical management. W.B. Saunders Company.

Ahn, H.J., et al., "Expression of cyclin E and cyclin–dependent kinase inhibitor, $p27^{kip1}$ in uterine endometrial carcinoma: relationship with p53 status," *International J. Surgical Pathology,* 1998, 6(4), 205–212.

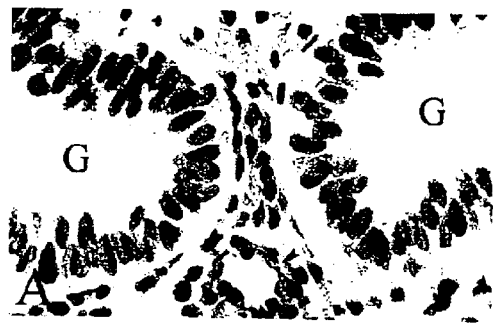
FIG. 3A　　　　　　FIG. 3B
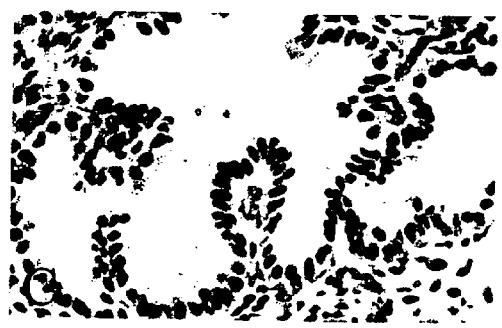
FIG. 3C　　　　　　FIG. 3D

METHODS OF DIAGNOSING AND MONITORING ENDOMETRIAL GLANDULAR DEVELOPMENT

CROSS-REFERENCE TO RELATED APPLICATIONS

The present application claims priority of application Ser. No. 60/187,682, filed Mar. 8, 2000, which is hereby incorporated by reference in its entirety.

FIELD OF THE INVENTION

The present invention relates generally to the fields of infertility, endometrial hyperplasia, assisted reproduction, and hormone replacement therapy for women, and methods of assessing and monitoring endometrial development in connection with diagnoses and therapies related to the same.

BACKGROUND OF THE INVENTION

Over 10% of reproductive age couples suffer from infertility. While many of these couples are successfully diagnosed and treated for their underlying conditions, nearly 20–25% are found to have no proven cause for their difficulties in achieving a successful pregnancy. Many of these couples further pursue costly procedures using assisted reproductive technology (ART) in an attempt to overcome their unidentified problems. The ART procedures used in the United States are IVF (in vitro fertilization), GIFT (gamete intrafallopian transfer), and ZIFT (zygote intrafallopian transfer). Yet, even with ART, only 29.5% of fresh, nondonor cycles result in pregnancies and only 24% result in live births. Rates vary between 19% and 25% depending on the cause of the infertility and older women generally have lower rates of success. Also, the live birth rate decreases to 18.6% when frozen embryos are used.

Clearly, despite improvements in embryo quality and culture conditions, some women are still unable to become pregnant. Their infertility, as well as the infertility experienced by many women, is likely caused in part by implantation difficulties. Thus, predictors of implantation potential are needed, both to better understand the causes of infertility in women and to improve the efficacy and reliability of embryo transfer. Despite over two decades of ART, no tools for endometrial evaluations exist which can adequately predict whether implantation will occur during any given ART cycle.

The Menstrual Cycle

The normal human menstrual cycle proceeds, on average, over the course of 28 days. However, menstrual cycle lengths in individual women vary considerably. For example, Trelar and his associates at the University of Minnesota found that three years after menarche, the range of menstrual intervals for 90% of the recorded cycles was 20.4 to 47.7 days. Their study, which analyzed 275,947 menstrual intervals recorded by more than 2700 women over extended periods, found similar variations during all periods of a woman's reproductive life. This variability is generally a reflection of the varying length of the follicular phase as opposed to the luteal phase, which lasts a relatively constant and predictable 14 days. While the length of a woman's menstrual cycle is rarely the idealized 28 days, investigations of the endometrium are based on this average 28 day cycle.

During the natural menstrual cycle, the normal human endometrium undergoes a hormone dependent cyclical series of changes, which involve the progression of proliferation to differentiation. Following menstruation, the endometrium enters the proliferative phase where, under the influence of estrogen, there is marked proliferation of epithelial and stromal cells as well as an increase in the length and tortuosity of the glands. These processes lead to an increase in endometrial thickness, culminating in a characteristic maximal 10–12 mm thickness at midcycle. Then, the luteinizing hormone (LH) surge on cycle day (CD) 13 causes ovulation to occur on CD 14. At this point the endometrium enters the secretory phase where, under the influence of progesterone, the endometrium differentiates, blood vessel and glandular tortuosity, as well as secretory activity, increases to a maximum and the stroma becomes edematous and increasingly vascular. It is during the middle of the secretory phase (CD 20–22) that the endometrium is best prepared for the trophoblast invasion portion of implantation. Estimates for the exact timing of the receptive period range from CD 17–19 to CD 20–24.

Histologic Evaluation of the Naturally Cycling Endometrium

The Noyes, Hertig and Rock Study

Histologically, there are a series of changes during the menstrual cycle that can be seen in the hematoxylin and eosin (H & E) stained endometrial slide. These changes in the histologic appearance of the endometrium were first described by Noyes, Hertig and Rock in 1950 and further elucidated several years later. In their study, "Dating the Endometrial Biopsy", Noyes and co-workers focused on the components which they felt changed most "rapidly, constantly, and characteristically" during the menstrual cycle. Those changes included features such as gland mitoses, pseudostratification of nuclei, basal vacuolization of gland cells, secretion into the gland lumen, the presence of stromal edema, stromal mitoses, and leukocyte infiltration. Based on their study of the temporal progression of each variable through a 28 day menstrual cycle and the cyclical changes in the histologic appearance of the endometrium, Hertig and co-workers proposed a method by which the endometrium could be dated within the menstrual cycle where the endometrium was assigned a date consistent with the most advanced component of the biopsy. They based the physiologic day on the date of ovulation, which they determined by the low end point of the first basal body temperature phase.

While Noyes et al. described a progressive series of changes in endometrial histology, their methods are neither necessarily appropriate for precise dating nor are they necessarily reflective of the normal, fertile endometrium. For example, they found that dating with their method was better correlated with the date of ovulation than with the onset of the next menstrual period. From this they concluded that the histologic evaluation was best suited to be a form of hormone assay intended to give a rough idea of quantitative progesterone effect, thus only indirectly indicating the time of ovulation and thus cycle day. This was a useful tool in 1950 to document ovulation—a tool that is secondary today to the documentation of the luteinizing hormone (LH) surge. Also, their findings were described as being applicable to what was referred to as "normal" endometrium. Subsequent clinical investigators as well as clinical practitioners have come to interpret this to mean normal fertile endometrium. However, most of the biopsies (percentages not given) were selected from sterility studies (from the hospital sterility clinic and the sterility practices of two staff members). Noyes and co-workers felt justified in claiming that these biopsies were representative of normally menstruating women because of an internal hospital report which claimed that 84.3% of the biopsies from these sterility patients were "normal."

Accuracy of the Noyes, Hertig and Rock Criteria for Endometrial Dating

Despite the limitations in using the Noyes et al. criterion to precisely date the normal, fertile endometrium, dating the endometrium using their criteria is used virtually exclusively by pathologists in both their clinical and experimental work. This reliance on what has come to be seen as the "gold standard" dating method is based on early evaluations such as the study by Noyes and Hamen in 1953. In this study, there was a reported agreement between two specially trained gynecopathologists of ±1 day in 82% of cases (i.e., if one pathologist assigned a biopsy as day 24, then another would interpret it as day 23, 24 or 25 82% of the time). Correlation was best in the middle and late secretory phases. Also, 80% of the histologic dates were found to be within 2 days of the physiologic date. Physiologic dating was determined by the midcycle change in basal body temperature (BBT) and the next menstrual period (NMP), which were found to bound a consistent 14.1 day secretory phase (standard deviation 1.7 days). In the 20% of cases where histologic and physiologic dates did not correlate the histologic dating tended to be earlier than the menstrual dating.

Although Noyes and Haman concluded from their study that histologically dating the endometrial was both useful and accurate, it is questionable whether a 82% interobserver agreement is adequate for a test meant to give precise dating information. Also, an analysis of the reasons for their reported interobserver variability deserves a second look. For example, in spite of the fact that the reporting pathologists were specially trained to histologically evaluate the endometrium, interobserver variability was reported to have occurred when slightly different criteria were used by the two pathologists. With an easy to use system, such variability should not have occurred. Particular difficulty was encountered when subnuclear glandular vacuoles were found in areas where the stroma appeared to be late secretory. (Glands with sub-nuclear vacuoles are consistent with the appearance of early secretory glands). Using the strict criterion of dating based on the most advanced portion of the biopsy, the presence of immature glands should not have affected the determination of an overall date.

The usefulness and accuracy of the original Hertig and Rock criteria to date the endometrial biopsy is further put into question when dating is done by pathologists not specially trained in gynecopathology or the particular criteria of dating the endometrial biopsy. As opposed to these specially trained professionals, the pathologists who read the endometrial biopsy for practicing clinicians, and whose reports are used both to guide clinical treatments and to serve as data for clinical studies, generally have no special interest in endometrial histology. When used by these individuals, the method has been shown to be imprecise with high levels of both inter and intra observer variability in its application.

Scott et al. investigated the effect of interobserver variation on the histologic dating of the endometrium with five pathologists, only one of whom was a gynecopathologist. In particular they examined the correlation between in-phase ($\leq 2$ days between physiologic date and endometrial date) and out-of-phase (>2 days between physiologic date and endometrial date) determinations in order to determine whether an alternate reading would lead to a change in management. Of note is the fact that the determination that a biopsy is greater than two days out of phase leads to a diagnosis of luteal phase defect. This diagnosis is confirmed by a second biopsy and leads to a luteal phase defect work-up. Out-of-phase was defined as a discrepancy of two or more days between histologic dating and the cycle date based on the patient's next menses. In their study they found that the probability of patient management being changed depending on the individual reading the biopsy was 39%. This, they concluded, was inappropriately high for a diagnostic test. Of note is the fact that they excluded several biopsies from the study which were found to have "severe dyssynchrony" between glands and stroma.

Later studies investigating the rates of inter as well as intra observer variability found rates similar to those reported by Scott et al. For example, Gibson et al. reported that 22% of readings done by two pathologists were discordant by >2 days and two readings done by the same pathologist on the same biopsy were discordant by $\geq 2$ days 17.6% of the time. Also, using the same criteria as Scott et al., Smith and co-workers found that 30% of the time a clinical management decision may be altered depending upon the interpreter of endometrial biopsy.

Optimizing the Histologic Evaluation of the Human Endometrium

Clearly it is problematic to date the endometrium using the original Hertig and Rock histologic criteria alone. Of particular interest is the fact the difficulties were often seen in both the original evaluation by Noyes and co-workers and by subsequent studies using non-gynecopathologists when there existed glands that appeared histologically delayed relative to the stroma (i.e., there was dyssynchrony between the development of the glands and of the stroma). This confusion over dealing with dyssynchronous biopsies indicates that rather than view the endometrial biopsy as a tool for determining a single date in the menstrual cycle, it may be necessary and appropriate to evaluate the stroma and glands separately based on the established progression of changes that occur in each compartment subsequent to the onset of the progesterone effect.

Biologically it makes sense to evaluate the glands and stroma as separate compartments of the endometrium. The two are of different embryologic origin: the glands are epithelial, the stroma is mesenchymal, and the two are separated by a basal lamina. The two have different endocrine functions: for example, only the stromal cells produce prolactin (PRL) and the stroma, more so than the glands, can make estrogens from androgens. The stroma and glands respond dissimilarly to estradiol and progesterone and each has an independent maturation process. In addition, research with endometrial culture has found that stroma and glands can grow individually in cell culture systems. These gland cultures and stromal cultures respond differently to hormonal therapy with estrogens and progesterone.

In addition to the biological basis for evaluating the development of the glands and stroma independently, there is evidence that such an analysis would be practically useful. For example, studies by several groups examined the endometrial biopsies of women with known fertility and elucidated a method of evaluating the endometrial biopsy by analyzing individual histologic features (morphometric analysis). These studies found that only a few of those features were needed to date the endometrium. Further, dating the endometrium using a morphometric analysis—as opposed to the traditional Hertig and Rock dating method—was, in fact, found to be more accurate. Accuracy in these studies was determined by the physiologic date relative to the LH surge and the date relative to well-defined hormonal events.

Other studies suggest that dyssynchrony may indicate an inadequate, implantation resistant endometrium. For example, Dockery et al., concerned with reports of inaccuracy in chronologically dating the endometrium, carried out a study utilizing morphometric analysis. In their study, endometrial biopsies of women with unexplained infertility were compared to those with known fertility. They found that by using a morphometric analysis women with unexplained infertility had a significant deviation from the normal range in five of the 14 features. All five features were related to glandular and not the stromal components of the endometrium and represented those biopsies whose glands were delayed relative to the stroma (dyssynchrony). This association between individual histologic features and unexplained infertility was significantly greater than the association found between overall retarded endometrial development (histologic dating) and infertility.

A practical approach for evaluating the endometrium which takes into account the independent development of the glands and stroma is presented by Hendrickson and Kempson. In their article, they give specific descriptions of the glands and stroma on each day of the standard 28 day menstrual cycle. They point out that exact dating can only be done on secretory phase endometrial samples which should be dated relative to the day of ovulation. They summarized their evaluations in a practical and easy to use decision tree for endometrial dating. In their decision tree, early secretory biopsies are distinguished based on the histologic appearance of the glands while mid and late secretory biopsies are identified by the stromal appearance. While the authors assert that the endometrium should be dated to a 48 hour period based on the most advanced portion of the biopsy (consistent with the original Hertig and Rock criteria), their detailed description of the glands and stroma allow their individual dating and thus the determination of dyssynchrony when present.

Endometrial Markers

The power of the histologic evaluation of the endometrium is limited by both the human factor and by the reality that H & E staining does not reveal biochemical cell differentiation events. Work has thus gone into trying to determine useful biochemical markers in order to both better understand and better diagnose endometrial abnormalities. While most of these markers have been investigated in the context of hyperplasia and malignancy investigations, some have also been used in the attempt to evaluate implantation resistant endometrium. Markers used in these infertility studies include estrogen and progesterone receptors, the $\alpha v \beta 3$ integrin, HOXA10, and MAG (Mouse Ascites Golgi).

Some of these markers have shown the potential for being clinically useful. For example, the $\alpha v \beta 3$ integrin is first found to be expressed in CD 19 biopsies (the first day in the presumed window of implantation) and both integrins and their ligands are found in the trophectoderm of the preimplantation blastocyst. This indicates that the $\alpha v \beta 3$ integrin may take part in the mechanisms underlying early events in implantation. Also, abnormalities in $\alpha v \beta 3$ integrin expression have been found in increased rates in states associated with decreased fertility such as endometriosis and hydrosalpinges as well as in women with unexplained infertility and in out-of-phase as opposed to in-phase biopsies. However, subsequent studies by other groups have had results which contradict the Lessey group's claims. For example, Creus, et al. found no difference in $\alpha v \beta 3$ integrin expression between women with and without endometriosis as well as between women who did and did not become spontaneously pregnant.

Progesterone receptors and assays to detect them are disclosed in Giangrande PH et al, The opposing transcriptional activities of the two isoforms of the human progesterone receptor are due to differential cofactor binding. Mol Cell Biol. 2000 May;20(9):3102–15; Mote PA et al., Colocalization of progesterone receptors A and B by dual immunofluorescent histochemistry in human endometrium during the menstrual cycle. J Clin Endocrinol Metab. 1999 August;84(8):2963–71; Wang H. et al., Progesterone receptor subtype B is differentially regulated in human endometrial stroma., Mol Hum Reprod. 1998 April;4(4):407–12.; Kumar NS et al., Selective down-regulation of progesterone receptor isoform B in poorly differentiated human endometrial cancer cells: implications for unopposed estrogen action. Cancer Research 1998 May 1;58(9):1860–5; Leslie K K et al., Differential expression of the A and B isoforms of progesterone receptor in human endometrial cancer cells. Only progesterone receptor B is induced by estrogen and associated with strong transcriptional activation. Annals of the New York Academy of Sciences 1997 Sep. 26; 828:17–26; and Mote PA et al., Colocalization of progesterone receptors A and B by dual immunofluorescent histochemistry in human endometrium during the menstrual cycle. J. Clin. Endocrinol. Metab. 1999 Aug;84(8):2963–71, which are each incorporated herein by reference.

Another potentially useful marker is MAG, a mucin related moiety found to be expressed by gland cells from CD 5–19. The correlation between its disappearance and the beginning of the window of implantation—as well as previous findings that mucin-lectin interactions take place between the conceptus and the endometrium during early implantation—implicate MAG in possibly having a role in mediating early implantation events. In addition, abnormal MAG mucin expression in natural cycle biopsies was found to predict pregnancy failures and abnormal expression in mock cycles was found to predict pregnancy failure in donor oocyte transfer cycles. U.S. Pat. No. 5,599,680, which is incorporated herein by reference discloses the use of MAG as a marker.

Despite their potential clinical usefulness, most of these markers have practical limitations to their use. For example, the anti-$\alpha v \beta 3$ integrin marker antibody used in the immunohistochemical investigations only works with frozen biopsies and not the more commonly retrieved formalin fixed, paraffin embedded sections. MAG, while it works well in these sections, and can thus be used in the examination of archival material, works only in the biopsies of blood group A individuals. HOXA10, as opposed to both $\alpha v \beta 3$ integrin and MAG, can not be evaluated with immunohistochemistry. Its expression is measured through the level of its RNA in frozen sections and thus can only be determined with special techniques that are not routinely performed in clinical pathology labs.

While a morphometric analysis of the endometrial biopsy provides a more objective measurement of endometrial development than the standard holistic process of assigning the biopsy a single CD, it is not necessarily the best practical solution for improving endometrial assessment as it is performed in clinical practice. The adoption of this system would require a shift in the paradigm used by pathologists to evaluate endometrial morphology. This might not be easily or consistently implemented. Further, even if it was possible to universally effect such a transformation, it would not necessarily be most efficient for a non-gynecopathologist to identify and then quantitate the appearance of dyssynchronous glands. A better solution might be to use markers of endometrial development; these would be both easy to interpret and easy to quantitate.

While markers investigated to date (such as the $\alpha v \beta 3$ integrin, HOXA10, and MAG) have shown promise in being clinically useful, each has a practical limitation. For example, the αvβ3 integrin can only be used in quick frozen samples and not in the more commonly retrieved formalin fixed, paraffin embedded sections. MAG works only in the biopsies of blood group A individuals. HOXA10 expression is measured through the level of its RNA in rapidly frozen tissue samples and thus can only be determined with special techniques that are not routinely performed in clinical pathology labs. Thus, informative markers are needed which can be used in the formalin fixed, paraffin embedded endometrial biopsies of all patients.

Regulators of Cell Cycle Progression as Endometrial Markers

While most of the biochemical markers investigated for evaluating the endometrium are products of the differentiated cell and thus reflect the cycle of changing differentiated function, it is also reasonable to hypothesize that the factors which regulate these changes in differentiation might be useful as endometrial markers. The endometrium typically undergoes highly regulated proliferation and differentiation changes every month. Passage of the endometrium through the menstrual cycle requires coordinated control of the endometrial cells through the cell cycle. Positive regulators of proliferation would thus be found in the estrogen driven first half of the menstrual cycle while inhibitors of proliferation, which would allow differentiation to occur, would be most commonly expressed in the progesterone supported second half of the menstrual cycle. Evaluation of the expression of these factors could therefore be useful in studying the normal progression of the endometrium through the menstrual cycle as well as to possibly identify endometrium that is abnormally progressing.

A family of these cell cycle regulators are the cyclins, their related cyclin dependent kinases (CDKs), and the cyclin dependent kinase inhibitors (CDKI). The cell's progression through the mitotic cycle is controlled by the activation and inactivation of, as well as the interactions between, these cyclins, CDKs and CDKIs. Overall, the cyclins positively regulate mitosis; the cyclins activate the CDKs, and the CDKs are inhibited by the CDKIs. CDKs also inhibit CDKIs. For example, the cyclin E-cdk2 complex is known to down regulate the CDKI, p27. Net control of mitosis is based on the relative levels of the cyclins, CDKs and CDKIs.

The G1 transition is controlled by a group of these cyclins, CDKs and CDKIs. Cyclin E and p27 in particular are critical regulators of the G1 to S transition. Cyclin E, a regulatory subunit of CDK-2, is thought to be rate limiting for the G1/S transition during the mammalian cell cycle. Its regulatory control is so strong that qualitative and quantitative alterations in cyclin E protein have been implicated as indicators of worse prognosis in various cancers. Conversely, p27 is a mitotic inhibitor which functions as a negative regulator of G1 progression and has been proposed to function as a possible mediator of TGFβ-induced G1 arrest. p27 is a candidate tumor suppressor gene.

Cyclin E and p27 have been shown to be clinically useful in the evaluation of malignant tissues. p27 has reduced expression in endometrial neoplasia and has been shown to have prognostic significance in human cancers. There are also indications that determining the subcellular localization of p27 is helpful. For example, p27 appears to interact with its targets in the cell nucleus and mislocalization of p27 in the cytoplasm might inactivate p27 by sequestering it away from relevant cellular targets. This cytoplasmic mislocalization of p27 has been reported in human tumors and cell lines, thus indicating that when p27 is in the cytoplasm it is inactive. Also, Soucek et al. found that p27 mislocalization in the cytoplasm resulted in a failure of p27 to inhibit the cell cycle, even when overexpressed.

Some previous studies have examined the changes in cyclin E and p27 expression during the menstrual cycle. Their focus was primarily the evaluation of hyperplasia and the effects of hormonal treatment. They found that more gland cells express cyclin E during the proliferative and early secretory phases than during the late secretory phase. Conversely, p27 expression was found to be negligible during the proliferative phase and markedly increased in the secretory phase. Some cyclin E positive secretory cells were found to express p27, suggesting an interaction between the two molecules. In addition, hyperplastic cells were found to have very low levels of p27. Levels were greatly increased after progesterone treatment. All findings indicated that expression changes of cyclins in the endometrium are likely controlled by the steroid hormones estrogen and progesterone.

While these studies confirmed that cyclin E and p27 are useful in distinguishing between the proliferative and secretory phases, their results are not directly useful for the evaluation of endometrial abnormalities such as glandular-stromal dyssynchrony. They did not evaluate the detailed progression of cyclin E and p27 expression nor their subcellular localization. Their biopsies did not necessarily reflect normal, fertile endometrium: while the biopsies came from women with a previous history of pregnancy, they were collected from hysterectomy specimens which were removed for either leiomyoma or carcinoma in situ of the uterine cervix. In addition, the authors either did not investigate or simply didn't distinguish biopsies which had internal glandular-stromal dyssynchrony and thus didn't report on the cyclin E and p27 staining patterns associated with this abnormality.

The standard infertility evaluation has classically included an endometrial assessment achieved through a histologic examination of the H & E stained biopsy. While many couples have achieved pregnancy through optimization of other aspects of the reproductive process—including anatomic evaluation, hormonal control, male factor analysis, and fertilization and embryo manipulation with ART—many women still do not become pregnant. In these, and other cases, implantation failure may underlie their infertility. Thus, an understanding of endometrial development is important to both help understand the reasons for the implantation failure and to facilitate the creation of easy-to-use methods for predicting endometrial receptivity.

Although endometrial assessment is important, and has a critical role in determining the cause of a woman's infertility, the tools available for this evaluation are limited in both their usefulness and accuracy. For example, the histologic examination, which is the most common evaluation method used by clinicians, is generally performed using the criteria of Noyes et al. where the endometrium is assigned a date consistent with the most advanced portion of the biopsy. Standard protocol involves comparing the reported date with the physiologic date (generally determined by the LH surge if known; otherwise by the next menstrual period). A discrepancy of greater than two days on two occasions is considered to be abnormal and prompts the diagnosis of a Luteal Phase Defect. Reports on the precision of this tool, however, show that it is actually insufficient for such a diagnostic test. Interobserver agreement of ±1 day is generally only found to be approximately 80%, even when the evaluation is performed by a trained gynecopathologist. This variation means that patient management can be changed simply depending on the individual reading the biopsy. Scott et al. reported this rate to be 39%. Clearly, a more objective diagnostic test for endometrial adequacy is needed.

As the techniques of assisted reproductive technology become more effective, an increasing number of patients are being identified who remain infertile due to implantation failure. However, there are still a limited number of tools to assess endometrial receptivity. Further, there is evidence that the tool most commonly used (the histologic examination of the H & E stained slide using the traditionally cited Hertig and Rock criteria) is insufficient as an absolute diagnostic tool in its level of detail, its degree of accuracy and its reproducibility.

There is a need to address the problems inherent in histologically evaluating the endometrial biopsy. There is a need for methods of endometrial biopsy evaluation that are easy to do, that use broadly applicable tools, and that provide more accurate and more uniform results than the methods of the past. The present invention is directed to addressing these, and other needs.

SUMMARY OF THE INVENTION

The present invention relates to methods of diagnosing an abnormality in endometrial glandular development in a woman suspected of being infertile. The methods comprise the step of detecting expression of cyclin E in the nuclei and/or the cytoplasm of endometrial gland cells in an endometrial tissue sample from on or after day 20 of an idealized 28 day menstrual cycle from a woman suspected of being infertile. Expression of cyclin E in the nuclei of greater than 5% of the gland cells indicates endometrial glandular developmental arrest. Expression of cyclin E of greater than 1+ staining intensity in the cytoplasm of greater than 10% of the gland cells indicates endometrial glandular developmental arrest.

The present invention further relates to methods of predicting abnormal endometrial glandular development. The methods comprise the steps of detecting the level of p27 in the nuclei of cells in a sample of endometrial tissue from day 10–18 of a an idealized 28 day menstrual cycle from a woman suspected of being infertile, and comparing the level of expression with an expected level of expression. Detection of elevated levels of p27 in the sample is predictive that the woman will be diagnosed with endometrial glandular developmental arrest.

The present invention further relates to methods of assessing the suitability of the endometrium for embryo implantation in a woman undergoing ovulation induction. The methods comprise the step of detecting expression of cyclin E in the nuclei and/or the cytoplasm of endometrial gland cells in an endometrial tissue sample from before day 17 of an idealized 28 day menstrual cycle. Expression of cyclin E in the nuclei of greater than 5% of the gland cells indicates the endometrium is unsuitable for embryo implantation. Expression of cyclin E of 2–3+ staining intensity in the cytoplasm of less than 50% of the gland cells indicates the endometrium is unsuitable for embryo implantation.

The present invention further relates to methods of evaluating the effect of a hormonal protocol on endometrial glandular development in a woman undergoing a hormonal protocol to produce a mock cycle. The methods comprise the step of detecting expression of cyclin E in the nuclei and/or the cytoplasm of endometrial gland cells in an endometrial tissue sample from on or after day 20 of an idealized 28 day menstrual cycle from a woman undergoing a hormonal protocol to produce a mock cycle. Expression of cyclin E in the nuclei of greater than 5% of the gland cells indicates endometrial glandular developmental arrest. Expression of cyclin E of greater than 1+ staining intensity in the cytoplasm of greater than 10% of the gland cells indicates endometrial glandular developmental arrest.

The present invention further relates to methods of evaluating a hormone replacement therapy protocol in a woman undergoing hormone replacement therapy. The method comprises the steps of detecting expression of cyclin E in the nuclei and/or the cytoplasm of endometrial gland cells in an endometrial tissue sample from said woman; and detecting expression of p27 in the nuclei an of endometrial gland cells in serial section of said endometrial tissue sample. Expression of cyclin E in the nuclei of greater than 5% of the gland cells indicates excessive estrogen. Expression of cyclin E of greater than 1+ staining intensity in the cytoplasm of greater than 10% of the gland cells indicates excessive estrogen. Expression of p27 in the nuclei of less than 20% of the gland cells indicates deficient progesterone.

The present invention further relates to methods of diagnosing endometrial glandular mitotic arrest in a woman suspected of having endometrial hyperplasia. The methods comprise the steps of detecting expression of cyclin E in the nuclei and/or the cytoplasm of endometrial gland cells in an endometrial tissue sample from said woman and detecting expression of p27 in the nuclei an of endometrial gland cells in serial section of said endometrial tissue sample. Expression of cyclin E in the nuclei of less than 10% of the gland cells and expression of p27 in the nuclei of greater than 10% of the gland cells indicates endometrial glandular mitotic arrest.

BRIEF DESCRIPTION OF THE DRAWINGS

FIG. 2A) Cyclin E expression in a mid proliferative gland demonstrates strong (3+) lateral cytoplasmic staining (membrane associated pattern). FIG. 2B) Approximate day 16 gland with increasing basal cytoplasmic staining (arrow heads). FIG. 2C) Isolated day 16–17 gland illustrates a continued increase in basal cellular cytoplasmic staining with a decreased presence in the lateral portions of the cytoplasm. FIG. 2D) Day 18–19 biopsy contains a CD 18–19 gland on the right and a CD 19 gland on the left. These gland cells which have residual cytoplasmic staining have minimal nuclear staining (arrows heads in CD 18–19 gland). In the CD 19 glands, cells without cytoplasmic staining have increased nuclear staining (arrows); FIG. 2E) late luteal (CD 24) glands (G) exhibit minimal cyclin E staining. FIG. 2F) Endothelial cells exhibit strong cytoplasmic staining (arrow heads) throughout the menstrual cycle. Magnification 400×, 2A–2F.

FIGS. 3A–3D shows immunohistochemical staining for p27 in the naturally cycling human endometrium. FIG. 3A) Prior to CD 19, trace nuclear and no cytoplasmic expression of p27 in the cells of the endometrial glands (G). Arrow heads show endothelial cells with strong cytoplasmic staining. FIG. 3B) CD 19 gland cells exhibit nuclear staining with the anti-p27 antibody. FIG. 3C and FIG. 3D) Late luteal gland cells have maximal p27 nuclear expression. Magnification 400×, 3A, 3B, 3D; 264×, 3C.

FIG. 4A) Biopsy sampled on CD 25 has primarily CD 25 glands with an occasional arrested mid-proliferative gland (MP) whose strong membrane patterned cyclin E cytoplasmic staining is consistent with its histologic dating. FIG. 4B) Biopsy sampled on CD 25 has primarily CD 25 glands with an occasional arrested CD 18–19 gland which exhibits strong cyclin E nuclear staining (arrow heads), typical of CD 19 glands. Magnification 264×, 4A, 4B.

DETAILED DESCRIPTION OF PREFERRED EMBODIMENTS

Definitions

Figure 1:
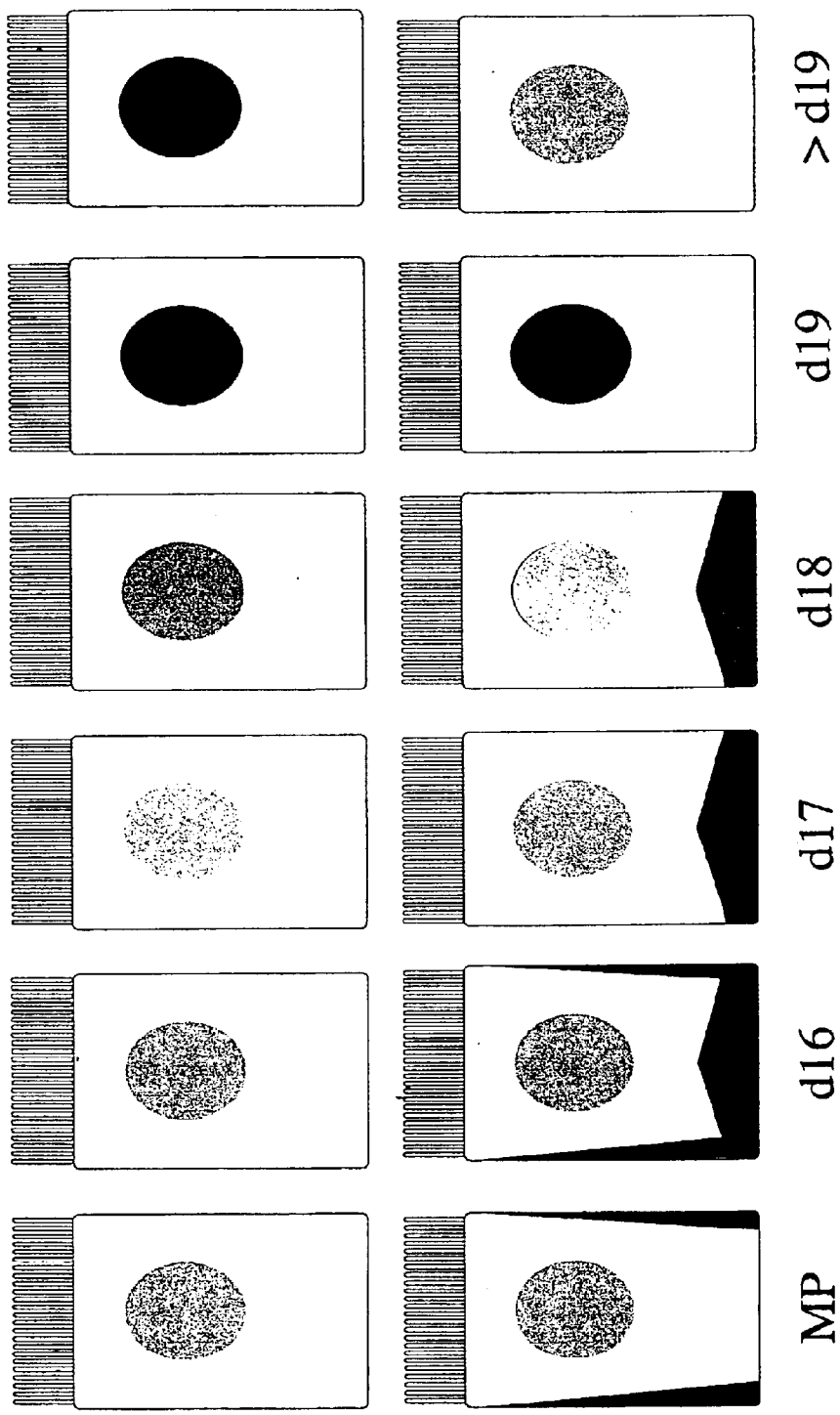
FIG. 1 diagrammatically depicts diagrammatically the immunostaining of cells through the normal menstrual cycle. Specific antibody staining is represented by the areas staining brown. Blue staining is from hematoxylin exposure. The top row of "cells" depicts p27 immunostaining. The bottom row of "cells" depicts cyclin E immunostaining.
Figure 2A:
FIGS. 2A–2F shows immunohistochemical staining for cyclin E in the naturally cycling human endometrium.
Figure 2B:
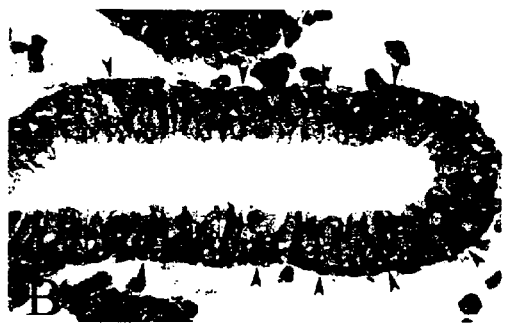
Figure 2C:
Figure 2D:
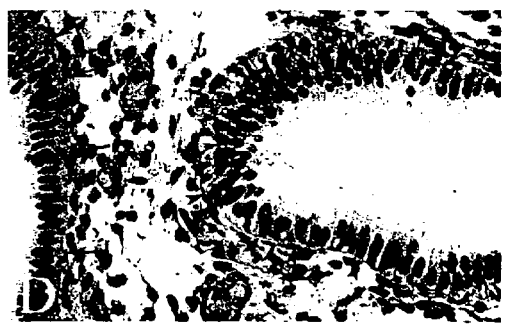
Figure 2E:
Figure 2F:
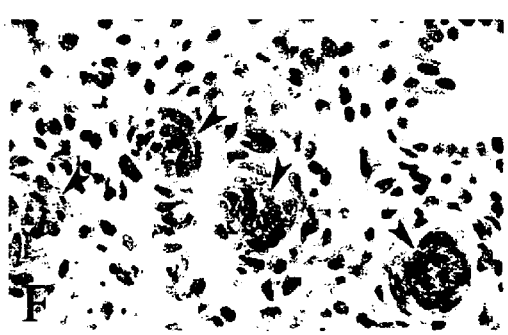

As used herein the phrase "abnormality in endometrial glandular development" is meant to refer to disorders and conditions characterized by abnormal development of endometrial gland cells such as endometrial glandular developmental arrest, accelerated endometrial glandular development, heterogenous endometrial glandular development and inadequate endometrial glandular development.

As used herein the phrase "endometrial glandular developmental arrest" is meant to refer the condition in which endometrial glandular development is dyssynchronous with endometrial stroma development and endometrial glands appear less developed than the endometrial stroma.

As used herein the system of "staining intensity in the cytoplasm" is the accepted standard for grading staining intensity in the field where a 0 to 3+ is used, 0 being no staining and 3+ being maximal staining.

As used herein cycle day is determined by examining the stroma and gland cells in the sample using the well accepted criteria set forth Noyes, R. W., A. T. Hertig, and Rock, J. (1950) Dating the endometrial biopsy, Fertil. Steril., 1:3–25 and Hendrickson, M. R., Kempson, R. L. (1980) Surgical pathology of the uterine corpus, *Major Problems Pathology* 12:36–98, which are each incorporated herein by reference.

As used herein, the phrase "an idealized 28 day menstrual cycle" is meant to refer to an objective reference of the theoretical 28 day cycle. It is well accepted that there may be some deviations from individual to individual with respect to the length of cycle. However, the relative benchmarks for the various days are essentially consistent when related to the 28 day cycle time. Those skilled in the art can, by the examination of stroma and glands, reconcile actual differences with the day markers for an idealized 28 day menstrual cycle. For example, in an idealized 28 day menstrual cycle ovulation occurs at day 14. If in the course of examining a patient ovulation was determined to occur on the 15$^{th}$ day following the start of the cycle, two days hence would be the 17$^{th}$ day following the start of the cycle but day 16 of an idealized 28 day menstrual cycle. Likewise, if ovulation was determined to occur on the 13$^{th}$ day following the start of the cycle, two days hence would be the 15$^{th}$ day following the start of the cycle but day 16 of an idealized 28 day menstrual cycle.

As used herein the phrase "serial section of the sample" is meant to refer to adjacent sections prepared from a single tissue sample.

As used herein, an expected level of nuclear expression of p27 at day 10–18 of an idealized 28 day menstrual cycle is 0 for day 10–16 and light to moderate staining (0.5+ to 1+) for day 17–18.

As used herein the phrase "suitability of the endometrium for embryo implantation" is meant to refer to the clinical determination that the development of the endometrial structures are appropriate and sufficiently advanced to support the implantation of an embryo coming into contact with it.

As used herein the phrase "a woman undergoing ovulation induction" refers to induction of ovulation including hyperstimulation by administration of pharmaceutical and/or biological agents. Examples of ovulation induction by administration of pharmaceutical and/or biological agents are set forth below.

As used herein the phrase "hormonal protocol to produce a mock cycle" refers to a hormonal regimen designed to mimic an idealized 28 day menstrual cycle by inhibiting the patient's hormone production and administering hormones according to a regimen designed to simulate the hormonal release in a normal cycle and the physiological affects including proper endometrial development, induced thereby.

As used herein the phrase "accelerated endometrial glandular development" is meant to refer to the condition in which endometrial glandular development is dyssynchronous with endometrial stroma development and endometrial glands appear more developed than the endometrial stroma or the cycle day as determined by LH surge or ovulation determined by ultrasound. Accelerated glandular development may be caused by too much hormonal stimulation leading to advanced maturation.

As used herein the phrase "inadequate glandular proliferation" refers to the abnormality of endometrial glandular development in which there is not enough estrogen or the response to estrogen is inadequate, or defective, or blocked.

As used herein the phrase "hormone replacement therapy" refers to the therapeutic protocols provided to peri and post menopausal women to provide them with estrogen replacement. The hormone replacement therapy referred to herein generally refers to that in which estrogen and progesterone or their analogs are administered concurrently.

As used herein the phrase "endometrial glandular mitotic arrest" is meant to refer the clinical diagnosis in which endometrial gland cells in an endometrial tissue sample appear by histological examination to be hyperplasic but which display biochemical markers which indicate the cells are in a non-dividing state.

Overview

It has been discovered that the expression patterns and cellular localization of the cellular protein cyclin E can be used as a marker to evaluate endometrial glandular development during the menstrual cycle. This marker is particularly useful when used in combination with the marker p27 and/or MAG and/or progesterone receptors. By detecting expression levels and cellular localization of markers at different time points in the menstrual cycle useful information can be gleaned and used in the diagnosis and treatment of patients being evaluated and treated for various conditions and disorders.

The present invention is useful in both diagnostic and monitoring applications. In some embodiments the discoveries underlying the present invention can be used to determine if a women who presents as infertile has abnormal endometrial glandular development while some embodiments assess expression patterns to determine if a woman who presents as having endometrial hyperplasia has endometrial glandular mitotic arrest as distinguished from hyperplasia associated with a hyperproliferative disease or condition. In some embodiments, the discoveries underlying the present invention make possible methods of determining whether the endometrium of a woman being induced to ovulate is developing in a manner suitable for implantation. Likewise, in some embodiments, the methods are useful to assess whether the hormone protocol being followed in the treatment of a woman undergoing a mock trial as part of assisted reproductive technology (ART) procedure is producing a cycle which resembles a normal cycle and is consistent with producing an endometrium that is suitable for embryo implantation. Adjustments to the protocol can be made based upon the assessment. Some embodiments of the invention relate to monitoring hormone replacement therapy protocols and making adjustments to protocols based upon evaluation results. In such embodiments, the expression patterns of the markers is different. Nonetheless the concept is similar in that both use the markers to provide a clearer understanding of the effects of the protocol including insight into adjustments to the protocol to achieve better therapeutic results.

Diagnosis of Abnormalities in Endometrial Glandular Development

In one aspect of the invention, the expression patterns and cellular localization of cyclin E is used to diagnose abnormalities in endometrial glandular development in women suspected of being infertile. Generally, when women present as being infertile and the basis of the diagnosis is undetermined, an evaluation of the expression patterns and cellular localization of the cellular protein cyclin E can be undertaken and used to determine if the patient suffers from endometrial glandular developmental arrest or other abnormalities of endometrial glandular development. When used in combination with evaluations of the expression patterns and cellular localization of other cellular proteins such as p27, and/or MAG and/or progesterone receptor, particularly at various time points, a diagnosis of abnormalities of endometrial glandular development in women suspected of being infertile can be made.

In one preferred embodiment, the method of diagnosing an abnormality in endometrial glandular development in a woman suspected of being infertile comprises the step of detecting expression of cyclin E in the nuclei and/or the cytoplasm of endometrial gland cells in an endometrial tissue sample from on or after day 20 of an idealized 28 day menstrual cycle from a woman suspected of being infertile. The expression of cyclin E in the nuclei of greater than 5% of the gland cells indicates endometrial glandular developmental arrest. Similarly, the expression of cyclin E of greater than 1+ staining intensity in the cytoplasm of greater than 10% of the gland cells indicates endometrial glandular developmental arrest.

In some embodiments, the expression of cyclin E is detected by an immunohistochemisty assay. Antibodies to cyclin E are well known, commercially available and can be made by those skilled in the art routinely. Likewise the preparation of the sample and the immunohistochemisty assay to be performed are well known and can be performed routinely by those skilled in the art.

In some embodiments, the expression of cyclin E and/or other markers is detected by an in situ hybridization assay to detect mRNA. Those skilled in the art can design probes which will be specific for mRNA encoding the markers based upon well known genetic sequences of the markers and routine design parameters. The detection of expression of markers may also be performed by any other methodology which allows for the detection and localization of specific protein or transcript of the markers.

In preferred embodiments, the sample obtained is from on or after day 20 of an idealized 28 day menstrual cycle. In some preferred embodiments, the sample obtained is from on day 20, 21, 22, 23, 24, 25, 26, 27, or 28 of an idealized 28 day menstrual cycle, more preferably day 23, 24 or 25, more preferably day 24.

The cycle day may be determined by any of several well known methods employed by those skilled in the art. In preferred embodiments, the cycle date is determined by examining the stroma cells in the sample and determining the date based upon their histological development.

As noted above, the expression of cyclin E in the nuclei of greater than 5% of the gland cells indicates endometrial glandular developmental arrest. In some embodiments, a diagnosis of endometrial glandular developmental arrest is made when the expression of cyclin E is detected in the nuclei of greater than 10% of the gland cells. In some embodiments, a diagnosis of endometrial glandular developmental arrest is made when the expression of cyclin E is detected in the nuclei of greater than 15% of the gland cells. In some embodiments, a diagnosis of endometrial glandular developmental arrest is made when the expression of cyclin E is detected in the nuclei of greater than 20% of the gland cells. In some embodiments, a diagnosis of endometrial glandular developmental arrest is made when the expression of cyclin E is detected in the nuclei of greater than 30% of the gland cells. In some embodiments, a diagnosis of endometrial glandular developmental arrest is made when the expression of cyclin E is detected in the nuclei of greater than 40% of the gland cells. In some embodiments, a diagnosis of endometrial glandular developmental arrest is made when the expression of cyclin E is detected in the nuclei of greater than 50% of the gland cells.

As noted above, the expression of cyclin E of greater than 1+ staining intensity in the cytoplasm of greater than 10% of the gland cells indicates endometrial glandular developmental arrest. In some embodiments, a diagnosis of endometrial glandular developmental arrest is made when the expression of cyclin E of greater than 1+ staining intensity is detected in the cytoplasm of greater than 15% of the gland cells. In some embodiments, a diagnosis of endometrial glandular developmental arrest is made when the expression of cyclin E of greater than 1+ staining intensity is detected in the cytoplasm of greater than 20% of the gland cells. In some embodiments, a diagnosis of endometrial glandular developmental arrest is made when the expression of cyclin E of greater than 1+ staining intensity is detected in the cytoplasm of greater than 30% of the gland cells. In some embodiments, a diagnosis of endometrial glandular developmental arrest is made when the expression of cyclin E of greater than 1+ staining intensity is detected in the cytoplasm of greater than 40% of the gland cells. In some embodiments, a diagnosis of endometrial glandular developmental arrest is made when the expression of cyclin E of greater than 1+ staining intensity is detected in the cytoplasm of greater than 50% of the gland cells.

In addition to detecting cyclin E expression and localization, the present invention relates to methods of detecting p27 and/or MAG and/or progesterone receptor expression to diagnose abnormalities of endometrial glandular development. In some embodiments, panels of two or more detection assays are performed. In some embodiments, the methods of diagnosing abnormalities of endometrial glandular development by detecting cyclin E expression patterns include the further step of detecting the expression of p27 in the nuclei of gland cells in a serial section of the sample. In some embodiments, the methods of diagnosing abnormalities of endometrial glandular development by detecting cyclin E expression patterns include the further step of detecting the expression of progesterone receptor in the gland cells in a serial section of the sample. In some embodiments, the methods of diagnosing abnormalities of endometrial glandular development by detecting cyclin E expression patterns include the further step of detecting the expression MAG in the gland cells in a serial section of the sample. In some embodiments, the methods of diagnosing abnormalities of endometrial glandular development by detecting cyclin E expression patterns include the further step of detecting the expression of p27 in the nuclei of gland cells in a serial section of the sample and either detecting the expression of progesterone receptor in the gland cells in a serial section of the sample or detecting the expression of MAG in the gland cells in a serial section of the sample or both. Panels which can be used to detect two or more of cyclin E, p27, progesterone receptor and MAG in serial sections are contemplated. Some preferred embodiments provide panels which can be used to detect three of cyclin E, p27, progesterone receptor and MAG in serial sections. In some preferred embodiments, panels are provided which can be used to detect each of cyclin E, p27, progesterone receptor and MAG in serial sections.

In addition to evaluations to be done on or after day 20, preferred embodiments include those methods in which an evaluation is performed on an endometrial tissue sample from on or before day 18 of an idealized 28 day menstrual cycle from the woman. In preferred embodiments, the evaluation is done on an sample from day 10, 11, 12, 13, 14, 15, 16, 17 or 18, preferable day 14, 15 or 16, more preferably day 15. In those embodiments which include assays done on samples from on or before day 18 of an idealized 28 day menstrual cycle from the woman and from on or after day 20 of an idealized 28 day menstrual cycle from the woman, the assay done on sample from on or before day 18 of an idealized 28 day menstrual cycle from the woman is referred to as the day 15 assay (even if the sample is dated 10, 11, 12, 13, 14, 16, 17 or 18) and the assay done on the sample from on or after day 20 of an idealized 28 day menstrual cycle from the woman is referred to as the day 24 assay (even if the sample is dated 20, 21, 22, 23, 25, 26, 27 or 28).

In some embodiments, the day 15 assay is used to detect cyclin E expression and localization, and/or p27 expression and localization and/or MAG expression and/or progesterone receptor expression. In some embodiments, the day 15 assay includes panels of two or more detection assays are perform. In some embodiments, the methods of diagnosing abnormalities of endometrial glandular development by detecting cyclin E expression patterns in a day 15 assay. In some embodiments, the methods of diagnosing abnormalities of endometrial glandular development by detecting p27 expression patterns in a day 15 assay. In some embodiments, the methods of diagnosing abnormalities of endometrial glandular development by detecting MAG expression patterns in a day 15 assay. In some embodiments, the methods of diagnosing abnormalities of endometrial glandular development by detecting progesterone receptor expression patterns in a day 15 assay.

In some embodiments, the methods of diagnosing abnormalities of endometrial glandular development include a day 15 assay which detects one or more of cyclin E, p27, MAG and progesterone receptor in serial sections of the sample. In some embodiments, the methods of diagnosing abnormalities of endometrial glandular development include a day 15 assay which detects two or more of cyclin E, p27, MAG and progesterone receptor in a serial sections of the sample. In some embodiments, the methods of diagnosing abnormalities of endometrial glandular development include a day 15 assay which detects cyclin E and p27 in a serial sections of the sample. In some embodiments, the methods of diagnosing abnormalities of endometrial glandular development include a day 15 assay which detects p27 and MAG in a serial sections of the sample. In some embodiments, the methods of diagnosing abnormalities of endometrial glandular development include a day 15 assay which detects cyclin E and MAG in a serial sections of the sample. In some embodiments, the methods of diagnosing abnormalities of endometrial glandular development include a day 15 assay which detects three of cyclin E, p27, MAG and progesterone receptor in a serial sections of the sample. In some embodiments, the methods of diagnosing abnormalities of endometrial glandular development include a day 15 assay which detects each of cyclin E, p27, MAG and progesterone receptor in a serial sections of the sample.

In some preferred embodiments, the day 15 assay is performed to detect p27 expression in a sample from before day 17 of an idealized 28 day menstrual cycle from the woman. The expression of p27 is indicative of accelerated endometrial glandular development. The preferred date of such an assay is day 15.

Because the information provided by this assay is particularly useful apart from any day 24 data, some embodiments of the present invention relate to methods of predicting abnormal endometrial glandular development comprising the steps of detecting the level of p27 in the nuclei of cells in a sample of endometrial tissue from day 10–18 of a an idealized 28 day menstrual cycle from a woman suspected of being infertile, and comparing the level of expression with an expected level of expression. The detection of elevated levels of p27 in the sample is predictive that the woman will be diagnosed with endometrial glandular developmental arrest. The expression of p27 is detected by an immunohistochemisty assay.

The cycle day, which may be any of day 10, 11, 12, 13, 14, 15, 16, 17 or 18, is preferably day 14, 15 or 16, most preferably day 15, and is preferably determined routinely by establishing that the stroma is not consistent with an endometrium from cycle days 20–28 and then examining the gland architecture, gland mitotic figures and percentage of gland cells with vacuoles and their subcellular localization. In some embodiments, the expression of cyclin E in the nuclei and/or cytoplasm of gland cells is detected in a serial section of the sample. In some embodiments, the expression of progesterone receptor in the gland cells in a serial section of the sample. In some embodiments, the expression of MAG in the gland cells in a serial section of the sample. In some preferred embodiments, the day 15 assay includes, in addition to the p27 assay, a panel detecting the expression of cyclin E in the nuclei and/or cytoplasm of the gland cells in an endometrial tissue sample from on or before day 18 of an idealized 28 day menstrual cycle from the woman and/or detecting expression of progesterone receptor in gland cells cells in an endometrial tissue sample from on or before day 18 of an idealized 28 day menstrual cycle from the woman; and/or detecting the expression of MAG in the gland cells in an endometrial tissue sample on or before day 18 of an idealized 28 day menstrual cycle from the woman; preferably at least two of the additional tests. In each case the tests are performed on serial sections of the sample.

Evaluation of Suitability of the Endometrium for Embryo Implantation

According to another aspect of the invention, the expression pattern and cellular localization of cyclin E can be used in methods of assessing the suitability of the endometrium for embryo implantation in a woman undergoing ovulation induction. In several assisted reproductive technology (ART) procedures, the induction of ovulation, including the hyperstimulation of the ovaries, is a component of the procedure. In such patients, the present invention can be used to assess the suitability of the endometrium for embryo implantation prior to the time when transfer is scheduled to occur. The present invention provides a basis to judge whether the conditions in the endometrium are unlikely to support implantation so that the transfer component of the procedure can be postponed. The suitability of the endometrium to support implantation, following the induction of ovulation and the potential disruption in endometrial development which may result form such induction, can be evaluated by the expression patterns and cellular localization of the cellular protein cyclin E alone or together with evaluations of the expression patterns and cellular localization of other cellular proteins such as p27, and/or MAG and/or progesterone receptor, particularly at a single or at various time points.

According to this aspect of the invention, the woman who is being monitored is undergoing ovulation induction as part of an ART procedure. In preferred embodiments, the ART procedure is selected from the group consisting of: IVF following hyperstimulation, IUI following clomiphene hyperstimulation; ZIFT following hyperstimulation and GIFT following hyperstimulation.

According to the methods of the invention which assess the suitability of the endometrium for embryo implantation in a woman undergoing ovulation induction, since the patient is contemplating undergoing a transfer or insemination the evaluation must be done before implantation, that is on an endometrial tissue sample from before day 17 of an idealized 28 day menstrual cycle. It is preferred that the sample is from day 10, 11, 12, 13, 14, 15 or 16, preferably day 14, 15 or 16, most preferably day 15.

In such methods, the detection of expression of cyclin E in the nuclei and/or the cytoplasm of endometrial gland cells in an endometrial tissue sample from before day 17 of an idealized 28 day menstrual cycle provides information regarding whether the endometrium is likely to provide suitable conditions, or at least that it is likely to be unsuitable. Expression of cyclin E in the nuclei of greater than 5% of the gland cells in an endometrial tissue sample from before day 17 indicates the endometrium is unsuitable for embryo implantation. Similarly, expression of cyclin E of 2–3+ staining intensity in the cytoplasm of less than 50% of the gland cells in an endometrial tissue sample from before day 17 indicates the endometrium is unsuitable for embryo implantation. The expression of cyclin E is preferably detected by an immunohistochemisty assay.

In some embodiments, the expression of cyclin E and/or other markers is detected by an in situ hybridization assay to detect mRNA. Those skilled in the art can design probes which will be specific for MRNA encoding the markers based upon well known genetic sequences of the markers and routine design parameters. The detection of expression of markers may also be performed by any other methodology which allows for the detection and localization of specific protein or transcript of the markers.

The cycle day may be determined by any of several well known methods employed by those skilled in the art. In preferred embodiments, the cycle date is determined routinely by establishing that the stroma is not consistent with an endometrium from cycle days 20–28 and then examining the gland architecture, gland mitotic figures and percentage of gland cells with vacuoles and their subcellular localization.

As noted above, the expression of cyclin E in the nuclei of greater than 5% of the gland cells indicates the endometrium is unsuitable for embryo implantation. In some embodiments, the conclusion that the endometrium is unsuitable for embryo implantation is determined when the expression of cyclin E is detected in the nuclei of greater than 10% of the gland cells. In some embodiments, the conclusion that the endometrium is unsuitable for embryo implantation is determined when the expression of cyclin E is detected in the nuclei of greater than 15% of the gland cells. In some embodiments, the conclusion that the endometrium is unsuitable for embryo implantation is determined when the expression of cyclin E is detected in the nuclei of greater than 20% of the gland cells. In some embodiments, the conclusion that the endometrium is unsuitable for embryo implantation is determined when the expression of cyclin E is detected in the nuclei of greater than 30% of the gland cells. In some embodiments, the conclusion that the endometrium is unsuitable for embryo implantation is determined when the expression of cyclin E is detected in the nuclei of greater than 40% of the gland cells. In some embodiments, the conclusion that the endometrium is unsuitable for embryo implantation is determined when the expression of cyclin E is detected in the nuclei of greater than 50% of the gland cells.

As noted above, the expression of cyclin E of 2–3+ staining intensity in the cytoplasm of less than 50% of the gland cells in an endometrial tissue sample from before day 17 indicates the endometrium is unsuitable for embryo implantation. In some embodiments, the conclusion that the endometrium is unsuitable for embryo implantation is determined when the expression of cyclin E of 2–3+ staining intensity in the cytoplasm of less than 40% of the gland cells in an endometrial tissue sample. In some embodiments, the conclusion that the endometrium is unsuitable for embryo implantation is determined when the expression of cyclin E of 2–3+ staining intensity in the cytoplasm of less than 30% of the gland cells in an endometrial tissue sample. In some embodiments, the conclusion that the endometrium is unsuitable for embryo implantation is determined when the expression of cyclin E of 2–3+ staining intensity in the cytoplasm of less than 20% of the gland cells in an endometrial tissue sample. In some embodiments, the conclusion that the endometrium is unsuitable for embryo implantation is determined when the expression of cyclin E of 2–3+ staining intensity in the cytoplasm of less than 10% of the gland cells in an endometrial tissue sample.

In addition to detecting cyclin E expression and localization, the present invention relates to methods of detecting p27 and/or MAG and/or progesterone receptor expression to diagnose abnormalities of endometrial glandular development. In some embodiments, panels of two or more detection assays are performed. In some embodiments, the assessment of suitability for implantation by detecting cyclin E expression patterns include the further step of detecting the expression of p27 in the nuclei of gland cells in a serial section of the sample. The expression of p27 in the nuclei of greater than 5% of the gland cells in the sample indicates the endometrium is unsuitable for embryo implantation. In some embodiments, the conclusion that the endometrium is unsuitable for embryo implantation is reached when expression of p27 is detected in the nuclei of greater than 10% of the gland cells in the sample. In some embodiments, the conclusion that the endometrium is unsuitable for embryo implantation is reached when expression of p27 is detected in the nuclei of greater than 20% of the gland cells in the sample. In some embodiments, the conclusion that the endometrium is unsuitable for embryo implantation is reached when expression of p27 is detected in the nuclei of greater than 30% of the gland cells in the sample. In some embodiments, the assessment of suitability for implantation by detecting cyclin E expression patterns include the further step of detecting the expression of progesterone receptor in the gland cells in a serial section of the sample. The expression of progesterone receptor in less than 20% of the gland cells in the sample indicates the endometrium is unsuitable for embryo implantation. In some embodiments, the conclusion that the endometrium is unsuitable for embryo implantation is reached when expression of progesterone receptor is detected in less than 10% of the gland cells in the sample. In some embodiments, the conclusion that the endometrium is unsuitable for embryo implantation is reached when expression of progesterone receptor is detected in less than 5% of the gland cells in the sample. In some embodiments, the assessment of suitability for implantation by detecting cyclin E expression patterns include the further step of detecting the expression of MAG in the gland cells in a serial section of the sample. The expression of MAG in less than 20% of the gland cells in the sample indicates the endometrium is unsuitable for embryo implantation. In some embodiments, the conclusion that the endometrium is unsuitable for embryo implantation is reached when expression of MAG is detected in less than 10% of the gland cells in the sample. In some embodiments, the conclusion that the endometrium is unsuitable for embryo implantation is reached when expression of MAG is detected in less than 5% of the gland cells in the sample. In some embodiments, the assessment of suitability for implantation by detecting cyclin E expression patterns include the further step of detecting the expression of p27 in the nuclei of gland cells in a serial section of the sample and either detecting the expression of progesterone receptor in the gland cells in a serial section of the sample or detecting the expression of MAG in the gland cells in a serial section of the sample or both. Panels which can be used to detect two or more of cyclin E, p27, progesterone receptor and MAG in serial sections are contemplated. Some preferred embodiments provide panels which can be used to detect three of cyclin E, p27, progesterone receptor and MAG in serial sections. In some preferred embodiments, panels are provided which can be used to detect each of cyclin E, p27, progesterone receptor and MAG in serial sections.

Evaluation of Endometrial Glandular Development in a Mock Cycle

According to a further aspect of the invention, the effect of the hormonal protocol used to produce a mock cycle on the endometrial glandular development in a woman undergoing the hormonal protocol can be evaluated to ensure that the hormonal protocol being followed produces a cycle which results in normal endometrial glandular development. In several ART procedures, a mock cycle is induced by disrupting the natural cycle and administering hormones to produce a controlled cycle. The mock cycle precedes the transfer cycle in which the natural cycle is again inhibited, and a controlled cycle is produced using administered hormones. During the transfer cycle, an embryo is delivered to the woman for implantation. According to the invention, the endometrial glandular development can be assessed during the mock cycle using expression patterns and cellular localization of the cellular protein cyclin E alone or together with evaluations of the expression patterns and cellular localization of other cellular proteins such as p27, and/or MAG and/or progesterone receptor, particularly at a single or at various time points. In addition, the hormonal protocol can be adjusted based upon the finding of the assessment to fine tune the protocol in an effort to produce a cycle which produces improved endometrial glandular development and more suitable conditions for implantation to occur following transfer.

In preferred embodiments of this aspect of the invention, the method of evaluating the effect of a hormonal protocol on endometrial glandular development and abnormal endometrial glandular development in a woman undergoing a hormonal protocol to produce a mock cycle, comprise the steps of detecting expression of cyclin E in the nuclei and/or the cytoplasm of endometrial gland cells in an endometrial tissue sample from on or after day 20 of an idealized 28 day menstrual cycle from the woman. In the mock cycle, day 14 of an idealized 28 day menstrual cycle corresponds to the date that progesterone is administered. The expression of cyclin E in the nuclei of greater than 5% of the gland cells indicates endometrial glandular developmental arrest, and/or the expression of cyclin E of greater than 1+ staining intensity in the cytoplasm of greater than 10% of the gland cells indicates endometrial glandular developmental arrest.

In some embodiments, the expression of cyclin E is detected by an immunohistochemisty assay. Antibodies to cyclin E are well known, commercially available and can be made by those skilled in the art routinely. Likewise the preparation of the sample and the immunohistochemisty assay to be performed are well known and can be performed routinely by those skilled in the art.

In some embodiments, the expression of cyclin E and/or other markers is detected by an in situ hybridization assay to detect mRNA. Those skilled in the art can design probes which will be specific for mRNA encoding the markers based upon well known genetic sequences of the markers and routine design parameters. The detection of expression of markers may also be performed by any other methodology which allows for the detection and localization of specific protein or transcript of the markers.

In preferred embodiments, the sample obtained is from on or after day 20 of an idealized 28 day menstrual cycle, that is on or after the $6^{th}$ day following progesterone administration. In some preferred embodiments, the sample obtained is from on day 20, 21, 22, 23, 24, 25, 26, 27, or 28 of an idealized 28 day menstrual cycle (6, 7, 8, 9, 10, 11, 12, 13 or 14 days after progesterone is initiated), more preferably day 23, 24 or 25 (9, 10 and 11 days post progesterone initiation), more preferably day 24 (10 days after progesterone is started).

The cycle day may be determined by any of several well known methods employed by those skilled in the art. In preferred embodiments, the cycle date is determined routinely by establishing that the stroma is not consistent with an endometrium from cycle days 20–28 and then examining the gland architecture, gland mitotic figures and percentage of gland cells with vacuoles and their subcellular localization.

As noted above, the expression of cyclin E in the nuclei of greater than 5% of the gland cells indicates endometrial glandular developmental arrest. In some embodiments, a diagnosis of endometrial glandular developmental arrest is made when the expression of cyclin E is detected in the nuclei of greater than 10% of the gland cells. In some embodiments, a diagnosis of endometrial glandular developmental arrest is made when the expression of cyclin E is detected in the nuclei of greater than 15% of the gland cells. In some embodiments, a diagnosis of endometrial glandular developmental arrest is made when the expression of cyclin E is detected in the nuclei of greater than 20% of the gland cells. In some embodiments, a diagnosis of endometrial glandular developmental arrest is made when the expression of cyclin E is detected in the nuclei of greater than 30% of the gland cells. In some embodiments, a diagnosis of endometrial glandular developmental arrest is made when the expression of cyclin E is detected in the nuclei of greater than 40% of the gland cells. In some embodiments, a diagnosis of endometrial glandular developmental arrest is made when the expression of cyclin E is detected in the nuclei of greater than 50% of the gland cells.

As noted above, the expression of cyclin E of greater than 1+ staining intensity in the cytoplasm of greater than 10% of the gland cells indicates endometrial glandular developmental arrest. In some embodiments, a diagnosis of endometrial glandular developmental arrest is made when the expression of cyclin E of greater than 1+ staining intensity is detected in the cytoplasm of greater than 15% of the gland cells. In some embodiments, a diagnosis of endometrial glandular developmental arrest is made when the expression of cyclin E of greater than 1+ staining intensity is detected in the cytoplasm of greater than 20% of the gland cells. In some embodiments, a diagnosis of endometrial glandular developmental arrest is made when the expression of cyclin E of greater than 1+ staining intensity is detected in the cytoplasm of greater than 30% of the gland cells. In some embodiments, a diagnosis of endometrial glandular developmental arrest is made when the expression of cyclin E of greater than 1+ staining intensity is detected in the cytoplasm of greater than 40% of the gland cells. In some embodiments, a diagnosis of endometrial glandular developmental arrest is made when the expression of cyclin E of greater than 1+ staining intensity is detected in the cytoplasm of greater than 50% of the gland cells.

In addition to detecting cyclin E expression and localization, the present invention relates to methods of detecting p27 and/or MAG and/or progesterone receptor expression when monitoring mock cycles to determine if abnormalities of endometrial glandular development are occurring. In some embodiments, panels of two or more detection assays are performed. In some embodiments, the methods of monitoring mock cycles by detecting cyclin E expression patterns include the further step of detecting the expression of p27 in the nuclei of gland cells in a serial section of the sample. In some embodiments, the methods of monitoring mock cycles by detecting cyclin E expression patterns include the further step of detecting the expression of progesterone receptor in the gland cells in a serial section of the sample. In some embodiments, the methods of monitoring mock cycles by detecting cyclin E expression patterns include the further step of detecting the expression MAG in the gland cells in a serial section of the sample. In some embodiments, the methods of monitoring mock cycles by detecting cyclin E expression patterns include the further step of detecting the expression of p27 in the nuclei of gland cells in a serial section of the sample and either detecting the expression of progesterone receptor in the gland cells in a serial section of the sample or detecting the expression of MAG in the gland cells in a serial section of the sample or both. Panels which can be used to detect two or more of cyclin E, p27, progesterone receptor and MAG in serial sections are contemplated. Some preferred embodiments provide panels which can be used to detect three of cyclin E, p27, progesterone receptor and MAG in serial sections. In some preferred embodiments, panels are provided which can be used to detect each of cyclin E, p27, progesterone receptor and MAG in serial sections.

In addition to evaluations to be done on or after day 20, preferred embodiments include those methods in which an evaluation is performed on an endometrial tissue sample from on or before day 18 of an idealized 28 day menstrual cycle from the woman (that is, on or before 4 days after progesterone is initiated). In preferred embodiments, the evaluation is done on an sample from day 14, 15, 16, 17 or 18, preferable day 14, 15 or 16, more preferably day 15. In those embodiments which include assays done on samples from on or before day 18 of an idealized 28 day menstrual cycle from the woman and from on or after day 20 of an idealized 28 day menstrual cycle from the woman, the assay done on sample from on or before day 18 of an idealized 28 day menstrual cycle from the woman is referred to as the day 15 assay (even if the sample is dated 14, 16, 17 or 18) and the assay done on the sample from on or after day 20 of an idealized 28 day menstrual cycle from the woman is referred to as the day 24 assay (even if the sample is dated 20, 21, 22, 23, 25, 26, 27 or 28).

In some embodiments, the day 15 assay is used to detect cyclin E expression and localization, and/or p27 expression and localization and/or MAG expression and/or progesterone receptor expression. In some embodiments, the day 15 assay includes panels of two or more detection assays are perform. In some embodiments, the methods of monitoring mock cycles by detecting cyclin E expression patterns in a day 15 assay. In some embodiments, the methods of monitoring mock cycles by detecting p27 expression patterns in a day 15 assay. In some embodiments, the methods of monitoring mock cycles by detecting MAG expression patterns in a day 15 assay. In some embodiments, the methods of monitoring mock cycles by detecting progesterone receptor expression patterns in a day 15 assay.

In some embodiments, the methods of monitoring mock cycles include a day 15 assay which detects one or more of cyclin E, p27, MAG and progesterone receptor in a serial sections of the sample. In some embodiments, the methods of monitoring mock cycles include a day 15 assay which detects two or more of cyclin E, p27, MAG and progesterone receptor in a serial sections of the sample. In some embodiments, the methods of monitoring mock cycles include a day 15 assay which detects cyclin E and p27 in a serial sections of the sample. In some embodiments, the methods of monitoring mock cycles include a day 15 assay which detects p27 and MAG in a serial sections of the sample. In some embodiments, the methods of monitoring mock cycles include a day 15 assay which detects cyclin E and MAG in a serial sections of the sample. In some embodiments, the methods of monitoring mock cycles include a day 15 assay which detects three of cyclin E, p27, MAG and progesterone receptor in a serial sections of the sample. In some embodiments, the methods monitoring mock cycles include a day 15 assay which detects each of cyclin E, p27, MAG and progesterone receptor in a serial sections of the sample.

In some embodiments, the methods of monitoring mock cycles include a day 15 assay which detects expression of p27 in the nuclei of endometrial gland cells in an endometrial tissue sample from before day 17 of an idealized 28 day menstrual cycle from the woman. The expression of p27 of greater than 2% is indicative of accelerated endometrial glandular development. In some embodiments, accelerated endometrial glandular development may be concluded if the expression of p27 is detected in greater than 5% of the nuclei of endometrial gland cells. In some embodiments, accelerated endometrial glandular development may be concluded if the expression of p27 is detected in greater than 10% of the nuclei of endometrial gland cells. In some embodiments, accelerated endometrial glandular development may be concluded if the expression of p27 is detected in greater than 5% of the nuclei of endometrial gland cells. In some embodiments, accelerated endometrial glandular development may be concluded if the expression of p27 is detected in greater than 2% of the nuclei of endometrial gland cells. In some embodiments, accelerated endometrial glandular development may be concluded if the expression of p27 is detected in greater than 0% of the nuclei of endometrial gland cells.

In some embodiments, the hormonal protocol is adjusted following evaluation, in an effort to alter the mock cycle to more closely resemble a natural cycle, if the monitoring method reveals that the mock cycle produced by the hormonal protocol deviates from the expression patterns produced by a normal cycle. In some embodiments, the subsequent mock trial with the adjusted hormonal protocol is monitored using the methods of the invention.

Evaluation of a Hormone Replacement Therapy Protocol

Similarly, another aspect of the present invention provides methods of evaluating hormone replacement therapy (HRT) protocols in a woman undergoing such therapy to achieve optimum beneficial effects and minimum undesirable side effects. The challenge of HRT protocols is to find the correct balance of estrogen and progesterone in order to confer the benefits of estrogen replacement while minimizing the risks associated with estrogen replacement. The concurrent administration of progesterone is used to minimize the harmful side effects of estrogen. However, progesterone causes symptoms and side effects which are themselves undesirable. The clinician can use aspects of the present invention to assess the effects of the HRT and adjust the protocol accordingly. In particular, expression patterns and cellular localization of the cellular protein cyclin E and p27 at a single or at various time points is useful to determine if the benefits of estrogen are being achieved with minimum side effects and doses of estrogen and progesterone. In some embodiments, evaluations of the expression patterns of MAG and/or progesterone receptor, at the single or various time points provide additional data for assessing the protocol being followed and making adjustments accordingly.

The goal in HRT is to achieve a state of endometrial stability with the least amount of estrogen and progesterone. Too much estrogen can be detected by a state of cyclin E positivity. Too much progesterone would show up as strong p27 staining. An inactive endometrium (ideal), would have minimal cyclin E and p27, maybe even both equally expressed.

In preferred embodiments of this aspect of the invention, the method of evaluating the effect of a HRT on endometrial glandular development and abnormal endometrial glandular development in a woman undergoing HRT, comprise the steps of detecting expression of cyclin E in the nuclei and/or the cytoplasm of endometrial gland cells in an endometrial tissue sample from the woman.

In some embodiments, the expression of cyclin E is detected by an immunohistochemisty assay. Antibodies to cyclin E are well known, commercially available and can be made by those skilled in the art routinely. Likewise the preparation of the sample and the immunohistochemisty assay to be performed are well known and can be performed routinely by those skilled in the art.

In some embodiments, the expression of cyclin E and/or other markers is detected by an in situ hybridization assay to detect mRNA. Those skilled in the art can design probes which will be specific for mRNA encoding the markers based upon well known genetic sequences of the markers and routine design parameters. The detection of expression of markers may also be performed by any other methodology which allows for the detection and localization of specific protein or transcript of the markers.

In addition to detecting cyclin E expression and localization, the present invention relates to methods of detecting p27 and/or MAG and/or progesterone receptor expression when HRT to determine if abnormalities of endometrial glandular development are occurring. In some embodiments, panels of two or more detection assays are performed. In some embodiments, the methods of monitoring HRT by detecting cyclin E expression patterns include the further step of detecting the expression of p27 in the nuclei of gland cells in a serial section of the sample. In some embodiments, the methods of monitoring HRT by detecting cyclin E expression patterns include the further step of detecting the expression of progesterone receptor in the gland cells in a serial section of the sample. In some embodiments, the methods of monitoring HRT by detecting cyclin E expression patterns include the further step of detecting the expression MAG in the gland cells in a serial section of the sample. In some embodiments, the methods of monitoring HRT by detecting cyclin E expression patterns include the further step of detecting the expression of p27 in the nuclei of gland cells in a serial section of the sample and either detecting the expression of progesterone receptor in the gland cells in a serial section of the sample or detecting the expression of MAG in the gland cells in a serial section of the sample or both. Panels which can be used to detect two or more of cyclin E, p27, progesterone receptor and MAG in serial sections are contemplated. Some preferred embodiments provide panels which can be used to detect three of cyclin E, p27, progesterone receptor and MAG in serial sections. In some preferred embodiments, panels are provided which can be used to detect each of cyclin E, p27, progesterone receptor and MAG in serial sections.

Evaluations may be done at two time points during HRT. In some embodiments, the HRT protocol is adjusted, following evaluation, to attempt to alter it so as to reduce side effects while maintaining beneficial effects. In some embodiments, a subsequent evaluation is done after the HRT protocol is adjusted.

Diagnosis of Endometrial Glandular Mitotic Arrest

In still another aspect of the invention, it has been discovered that expression patterns and cellular localization of the cellular protein cyclin E and p27can be used to diagnose endometrial glandular mitotic arrest in a woman suspected of having endometrial hyperplasia. In particular, a subset of women who present with symptoms suggesting endometrial hyperplasia do not have endometrial hyperplasia associated with carcinoma or another hyperproliferative condition. Rather, endometrial glandular mitotic arrest can lead to similar symptoms. Moreover, both endometrial glandular mitotic arrest and endometrial hyperplasia associated with carcinoma or another hyperproliferative condition can be indistinguishable or difficult to distinguish by histological examination of biopsy samples. According to the present invention the expression patterns and cellular localization of the cellular proteins cyclin E and p27 are useful to diagnose endometrial glandular mitotic arrest and distinguish it from endometrial hyperplasia associated with carcinoma or another hyperproliferative condition.

According to this aspect of the invention, methods of diagnosing endometrial glandular mitotic arrest in a woman suspected of having endometrial hyperplasia are provided which comprise the steps of detecting expression of cyclin E in the nuclei and/or the cytoplasm of endometrial gland cells in an endometrial tissue sample from said woman and detecting expression of p27 in the nuclei an of endometrial gland cells in serial section of said endometrial tissue sample. The expression of cyclin E in the nuclei of less than 10% of the gland cells and expression of p27 in the nuclei of greater than 10% of the gland cells indicates endometrial glandular mitotic arrest. In preferred embodiments, the expression of cyclin E and p27 is detected by an immunohistochemisty assay. In some embodiments, the woman has been diagnosed as having endometrial hyperplasia by histological evaluation of a sample of endometrial tissue.

In some embodiments, the expression of cyclin E and/or p27 and/or other markers is detected by an in situ hybridization assay to detect mRNA. Those skilled in the art can design probes which will be specific for mRNA encoding the markers based upon well known genetic sequences of the markers and routine design parameters. The detection of expression of markers may also be performed by any other methodology which allows for the detection and localization of specific protein or transcript of the markers.

Endometrial glandular mitotic arrest is characterized by simultaneous low or no cyclin E and moderate or high levels of p27. This is directly the opposite of what has been claimed to be the pattern seen in hyperproliferating hyperplasias such as endometrial adenocarcinoma.

As noted above, the expression of cyclin E in the nuclei of less than 10% of the gland cells and expression of p27 in the nuclei of greater than 10% of the gland cells indicates endometrial glandular mitotic arrest. In some embodiments, a diagnosis of endometrial glandular mitotic arrest is made when the expression of cyclin E is detected in the nuclei of less than 20% of the gland cells. In some embodiments, a diagnosis of endometrial glandular mitotic arrest is made when the expression of cyclin E is detected in the nuclei of less than 30% of the gland cells. In some embodiments, a diagnosis of endometrial glandular mitotic arrest is made when the expression of cyclin E is detected in the nuclei of less than 40% of the gland cells. In some embodiments, a diagnosis of endometrial glandular mitotic arrest is made when the expression of cyclin E is detected in the nuclei of less than 50% of the gland cells.

In some embodiments, a diagnosis of endometrial glandular mitotic arrest is made when expression of p27 is detected in the nuclei of greater than 20% of the gland cells. In some embodiments, a diagnosis of endometrial glandular mitotic arr est is made when expression of p27 is detected in the nuclei of greater than 30% of the gland cells. In some embodiments, a diagnosis of endometrial glandular mitotic arrest is made when expression of p27 is detected in the nuclei of greater than 40% of the gland cells. In some embodiments, a diagnosis of endometrial glandular mitotic arrest is made when expression of p27 is detected in the nuclei of greater than 50% of the gland cells.

While the disclosure herein primarily relates to uses of the methods of the present invention for diagnosing and monitoring humans, the methods of the present invention can be applied to veterinary medical uses too. It is within the scope of the present invention to provide methods of diagnosing and monitoring non-human as well as human individuals. Accordingly, the present invention includes methods of diagnosing and monitoring endometrial development in mammals. The methods of the present invention can be particularly useful for mammalian species including human, bovine, ovine, porcine, equine, canine, lupine and feline species as well as other mammalian species common in zoological collections which are subject to ART and reproductive evaluation. The cycle days set forth in the disclosure for human menstrual cycle can be routinely converted to the cycle days for non-human mammals.

The Examples set out below include representative examples of aspects of the present invention. The Examples are not meant to limit the scope of the invention but rather serve exemplary purposes. In addition, various aspects of the invention can be summarized by the following description. However, this description is not meant to limit the scope of the invention but rather to highlight various aspects of the invention. One having ordinary skill in the art can readily appreciate additional aspects and embodiments of the invention.

EXAMPLES

Example 1

Materials and Methods

Endometrial Biopsies

The use of archival pathology materials in this study was approved by the Yale University Human Investigations Committee. Each specimen had been obtained by Pipelle sampling from the uterine cavity and was immediately fixed in 10% phosphate-buffered formalin for at least 24 h and embedded in paraffin. Three sets of endometrial biopsies were collected.

1. Samples of endometrial biopsies used to evaluate inter-observer variability: 68 biopsies from women being treated for infertility were used to evaluate interobserver variability between the gynecopathologist who evaluated the endometrial biopsies for this study and three commercial pathology laboratories. These early and late luteal phase (cycle days (CD) 15–19 or 23–27) biopsies were collected from a private infertility practice. (Biopsy specimens at the commercial laboratories were evaluated by 7 different pathologists). These biopsies represent a random sample of patients with various reasons for their infertility.

2. Normal/Fertile endometrial samples: 22 biopsies of normal fertile endometrium were collected from 14 volunteers and 2 tubal ligation patients from the mid proliferative through the late secretory phases of the menstrual cycle. All patients were 25–35 years old and all had a parity of at least one.

3. Biopsies of infertility patients: 76 biopsies were collected from 53 women in the proliferative phase or in either the early or the late luteal phases. 40 of these biopsies were sampled from 23 women during an artificially stimulated cycle prior to donor oocyte implantation. 36 of these biopsies from 30 naturally cycling women were from a random sampling of infertility patients whose biopsies were previously taken as part of their infertility work-up.

Endometrial Dating

Standard hematoxylin and eosin stained sections were examined for dating. Histological diagnosis and endometrial dating of the stroma and glands was performed according to the general criteria of Noyes et al., as more fully detailed in Hendrickson and Kempson's Decision Tree for Endometrial Dating. As described by these authors, only the portions of each biopsy from the functional is layer were used for dating. Both the stroma and the glands were dated independently and the percent of glands whose appearance was consistent with a date other than the date applied to the stroma (i.e., the dyssynchronous glands) were recorded.

Analysis of Interobserver Variability

Sixty eight endometrial biopsy readings from two commercial pathology laboratories used by a private infertility clinic were compared to the evaluation of the same biopsies performed a gynecopathologist. The histologic date and frequency of dyssynchrony reported was compared to that reported by the commercial laboratories. Given that the single date assigned to an endometrial biopsy by the traditional Hertig and Rock criteria is supposed to correspond to the date of the most advanced portion of the biopsy and the fact that in 100% of the biopsies with dyssynchrony the stroma was the most advanced portion, the frequency distribution between a single designated histologic date determined by the commercial pathology laboratories was compared to the stromal date determined when dyssynchrony was deemed to be present.

Immunohistochemistry

Serial sections (5 μm) from the formalin fixed, paraffin embedded biopsies were placed on glass slides previously coated with a film of 1% poly-d-lysine, 30,000 to 70,000 molecular weight (Sigma), dried for 30 minutes at temperatures no greater than 60 C. and stored at room temperature until used. Indirect immunostaining was performed using anti-cyclin E and anti-p27 antibodies. The antibody for cyclin E (clone HE12) and p27 (clone DSC-72.F6) were purified mouse monoclonal antibodies type IgG1, purchased from NeoMarkers (Lab Vision Corp., Fremont, Calif.).

Immunoperoxidase staining was performed by the avidin-biotin detection method with kits from Vectastain with diaminobenzidine (DAB) as the chromagen. After deparaffinization in xylene and rehydration through graded concentrations of alcohol, each section was treated by heating in a microwave in 0.01 M citrate buffer (pH 6.0). This heating step proved to be critical and optimal results were obtained only when the buffer was allowed to fully boil for 5 minutes (with occasional fluid replacement for evaporation losses). The samples were then allowed to cool at room temperature for 1 hour. Next, endogenous peroxidase activity was blocked by 0.6% hydrogen peroxide in methyl alcohol for 15 minutes. Following a wash in phosphate buffered saline/bovine serum albumin (PBS/BSA) slides were incubated with blocking serum (horse) to minimize non-specific reactions. Sections were then incubated with specific primary antibodies (diluted 1:100 with PBS/BSA for anti-cyclin E and 1:800 with PBS/BSA for anti-p27) at 4° C. overnight. After rinsing with PBS, biotinylated anti-mouse IgG was applied for 30 minutes at room temperature. After rinsing again with PBS, an avidin and biotinylated peroxidase solution was applied for 45 minutes at room temperature and the antigen-antibody reaction was visualized by diaminobenzidine (DAB). The tissue was counterstained with hematoxylin.

Interpretation of Immunohistochemical Staining

The specific staining of cyclin E and p27 was identified by the presence of brown-colored products in the nucleus and/or cytoplasm. Negative control slides, which were slides stained with non-immune mouse ascites (NMA), yielded negative staining. Biopsies that were shown to be strongly positive were utilized as positive controls for subsequent studies. These positive control slides repeatedly yielded positive staining. Endothelial cells (i.e., vascular cells) were found to act as an internal positive control for cytoplasmic staining on each slide. Staining within the glands and the stroma was evaluated separately. Overall the process of evaluating the immunohistochemical staining can be easily taught to any pathologist independent of specialized training in gynecopathology.

Gland Staining

Within the glands, the percent of cells with the nuclei stained and the percent of glands with positively stained cytoplasm were visually assessed. A score was assigned to each to reflect the intensity of the staining (ranging from 0 for none, +0.5 for the least and +3 for the most intense staining). Cytoplasmic staining was further categorized based on the location of the staining. Staining along the lateral sides of the cells was designated as a membrane pattern. Staining in the basal portion of the gland cells was designated as a basal pattern.

Stroma

As with the glands, within the stroma the percent of cells with the nuclei stained and the percent of cells with the cytoplasm stained were visually assessed. A score was assigned to each to reflect the intensity of the staining (ranging from 0 for none, +0.5 for the least and +3 for the most intense staining). The presence or absence of endothelial cell staining was also recorded.

Scoring Dyssynchrony

Glands whose staining pattern did not correlate with the dating of the stroma were further analyzed. The label of regional staining was applied when the glands with the non-appropriate staining were found to be localized to one region of the biopsy. The label of differentiation specific expression (DSE) was applied when the dyssynchronous glands (i.e., glands appeared to be at a different CD than the surrounding stroma) had staining patterns consistent with their apparent morphologic date.

Example 2

Correlation Between Evaluations of Clinical Pathology Lab and Gynecopathologist

It was found that 51 of 60 (85%) mid to late luteal phase biopsies (CD22–26) had some degree of dyssynchrony. Of these biopsies, 5 had 1–10% dyssynchronous glands, 14 had 11–40% dyssynchronous glands, 10 had 41–70% dyssynchronous glands and 22 had 71–100% dyssynchronous glands. The commercial pathology laboratories reported that only 4 of 60 (6.7%) of these biopsies had dyssynchronous glands. While no percentage of dyssynchronous glands were reported by the commercial lab, these four biopsies were assessed as having 15%, 70%, 80% and 100% dyssynchronous glands.

A comparison of the final cycle day assigned to each biopsy and the commercial laboratories revealed that 43% differed by ≧2 days and, remarkably, 15% differed by >4 days. Of these 15%, all had dyssynchrony and all had the date designated by the commercial laboratory consistent with the glandular dating assigned earlier.

In this study we attempted to understand some of the difficulties with using the Noyes et al. criteria for endometrial assessment. For our analysis, we compared the biopsy reports from a pathology center used by a private infertility clinic to the morphometric analyses of mid to late secretory endometrial biopsies (CD 22–27). Most endometrial biopsies for the infertility work-up are sampled during this mid to late secretory period. Our morphometric analysis involved dating the glands and the stroma separately and determining the percentage of glands whose morphologic CD did not correspond to that of the apparent CD of the stroma.

Our investigation showed that the commercial labs underreported the presence of dyssynchrony. While it was reported that 85% of the biopsies had dyssynchrony, a rate of only 7% was reported by the commercial pathology labs. These 7% (or 4 out of 60 biopsies) were not all the biopsies reported to have the highest levels of dyssynchrony. Thus, a designation of dyssynchrony was inconsistently applied by the commercial labs and did not reflect a more significant degree of dyssynchrony.

In addition to the differences in reported dyssynchrony, there was significant interobserver variation between the readings produced and those by the commercial pathology labs. Given that the standard Hertig and Rock method of endometrial dating dictates that the endometrium be assigned a date consistent with the most advanced portion of the biopsy and the fact that the stroma consistently dated more advanced than the glands when there was dyssynchrony present, the date assigned by the commercial lab was compared to the stromal dating assigned by us. The finding was that only 57% of the biopsies were concordant by less than 2 days. Of note is the fact that 15% of the biopsies had significant discordance between the two readings (greater than 4 day). All dates assigned by the commercial laboratory to these biopsies corresponded to the date assigned by us to the dyssynchronous glands, thus indicating that the commercial pathology lab dated the biopsies through an evaluation of the glandular developmental stage, while ignoring the stroma.

Overall, these results suggest that a subjective evaluation is insufficient for endometrial assessment and is a source of significant error and interobserver variability. It also often gives an incomplete report of endometrial development. It might thus be better to replace this method with more objective measurements of endometrial maturation.

Example 3

Cyclin E and p27 Expression in Endometrial Biopsies of Normal Fertile Women

Immunohistochemical staining of mid-proliferative (MP) through late secretory endometrial biopsies revealed a progressive series of changes in the expression and sub-cellular location of both cyclin E and p27 in the endometrial glands. This is represented diagrammatically in FIG. 1. Stromal expression of neither cyclin E nor p27 changed appreciably during the menstrual cycle. The cytoplasm of endothelial cells stained consistently and intensely (3+) with both the cyclin E and the p27.

Cyclin E Expression

Using the anti-cyclin E antibody, the sub-cellular distribution of cyclin E in the endometrial gland cells throughout the menstrual cycle was examined. Immunohistochemical staining for cyclin E in the naturally cycling human endometrium reveals a dynamically changing pattern of sub-cellular localization in the glands throughout the menstrual cycle (standardized to 28 days). Expression of cyclin E in cells from the MP glands exhibited strong basal and lateral cytoplasmic staining (see top row of FIG. 1). From CD 16 to 17 the cytoplasmic lateral staining decreased while the basal staining increased. From CD 18 to 19 there was a reciprocal pattern of decreasing cytoplasmic and increasing nuclear staining. CD 24 to 28 biopsies revealed only trace nuclear staining.

Details of the immunohistochemistry for cyclin E can be seen in FIG. 2. The mid proliferative (MP) gland cells exhibit strong (approximately 3+ intensity) lateral cytoplasmic staining (FIG. 2A). This pattern is referred to as a "membrane associated pattern." From CD 16 to 17 the endometrial gland cells have decreased lateral cytoplasmic and increased basal staining relative to the MP cells (FIGS. 2B, 2C). From CD 18 to 19 there is a reciprocal pattern of decreasing cytoplasmic and increasing nuclear staining. CD 19 biopsies exhibit maximal nuclear staining (FIGS. 2D, 2E). Late luteal (CD 24) glands (G) exhibit minimal cyclin E staining (FIG. 2E). CD 23 to 27 biopsies revealed only trace nuclear staining (FIG. 2F).

p27 Expression

Immunohistochemical staining for p27 in the naturally cycling human endometrium reveals a dynamically changing pattern of sub-cellular localization in the glands throughout the menstrual cycle (standardized to 28 days) (see FIG. 1, bottom row, for diagram of staining of individual cells, and FIG. 3 for the immunohistochemistry photos).

Using the anti-p27 antibody, the sub-cellular distribution of p27 in the endometrial gland cells throughout the menstrual cycle was found to be as follows. As with the cyclin E studies, there is strong p27 staining in the endothelial cell cytoplasm throughout the menstrual cycle (note the strong endothelial cell cytoplasmic staining (arrow heads) in FIG. 3A). Trace nuclear and no cytoplasmic staining was noted in MP to CD 16 endometrial glands (G) in the biopsies (FIG. 3A). Nuclear p27 staining progressively increased from CD 17 to CD 19 (FIG. 3B). In CD 23 to 27 endometria, late luteal gland cells have maximal p27 nuclear expression (FIGS. 3C, 3D). The onset and subsequent increase of p27 expression corresponds to both the decrease in the expression of cyclin E and the onset of the progesterone effect during the luteal phase.

Discussion

Given that the endometrium undergoes a cyclic progression of proliferation and differentiation every menstrual cycle, we postulated that mitotic cycle regulators that underlie these changes might be useful in evaluating endometrial development. Through an evaluation of a series of antibodies against these regulators—specifically cyclins, cyclin dependent kinases (CDKs), and cyclin dependent kinase inhibitors (CDKIs), as well as topoisomerase II and the apoptosis regulator bc1–2—we found that the monoclonal antibodies against cyclin E and the CDKI p27 were the most useful. Each worked well in formalin-fixed, paraffin embedded sections and further, each yielded a staining pattern which consistently progressed through the menstrual cycle.

In order to determine the normal patterns of cyclin E and p27 expression, we collected a series of 22 biopsies from women with known fertility. Through our investigations we found that glandular changes in expression were most informative. As opposed to the glands, the stroma had a relatively consistent cyclin E and p27 expression through the menstrual cycle. We were unable to determine the progression of surface expression because most biopsies had either no, or not enough, surface present for a sufficient evaluation. The progression of changes in glandular expression are diagrammed in FIG. 1. Cyclin E essentially progressed from the lateral cytoplasm (proliferative), to the basal cytoplasm (CD16–17), to the nucleus (CD 18–19), to no expression (mid to late proliferative). Alternatively, p27 first appeared in the nucleus CD 18–19 and was found to be strongly expressed in the nucleus in the mid and late secretory phases.

These patterns of cyclin E and p27 expression are logical, fitting with their known mechanisms of action. The proliferative and early secretory phases of the menstrual cycles are controlled by estrogens which are mitogenic for uterine epithelial cells (the glandular and surface cells). Estrogens work by stimulating progression of the cell through the G1 phase. This progression is accomplished through the activation of the G1 cyclins, including cyclin E. Hence, it is logical to find cyclin E in the proliferative and early secretory phases of the menstrual cycle. Progestins, which control the mid and late secretory phases, promote differentiation by halting mitotic progression through the G1 phase. They work by promoting the expression of CDKIs which are active when located in the cell nucleus. CDKIs initially halt G1 progression by complexing with, and thus inactivating, the cyclin/CDK complex. Further, control is effected through downregulating the expression of the cyclin and/or CDK genes. Also, progestins themselves both stimulate the CDKI/cyclin/CDK association and down regulate cyclin expression. Hence, it is logical to find cyclin E/p27 coexpression in progestin controlled CD18–19 gland nuclei, where p27 is likely inhibiting cyclin E activity. As well, it makes sense to see p27 nuclear expression without cyclin E in the differentiated mid to late secretory biopsies, where p27, as well as progesterone, likely inhibits cyclin E production.

In addition to being expressed in the glands and stroma, both cyclin E and p27 were found in the endothelial cells. The cytoplasm of these endothelial cells, which make up the walls of the endometrial vasculature, stained maximally for both cyclin E and p27 through all phases of the menstrual cycle. This expression was found to be so consistent that the endothelial cells were used as internal controls for cytoplasmic staining. A search of the literature did not yield an explanation for this finding. However, this cyclin E and p27 cytoplasmic expression is consistent with what one might expect to find in proliferating cells such as the endometrial blood vessels which continue to divide throughout the menstrual cycle. For example, the cytoplasmic expression of cyclin E may reflect its positive activity, just as cyclin E was found in the cytoplasm of proliferating gland cells. Conversely, the p27 cytoplasmic localization indicates that the p27 is inactive—also what is expected in proliferating cells. In addition, there was no evidence from our studies, or the literature, that either the HE12 cyclin E antibody clone or the DCS-72.F6 p27 antibody clone used here exhibited non-specific binding. Further investigations into the reasons for this endothelial expression are needed.

Example 4

Cyclin E and p27 Expression in Dyssynchronous Endometrial Biopsies

Figures 4A, 4B:
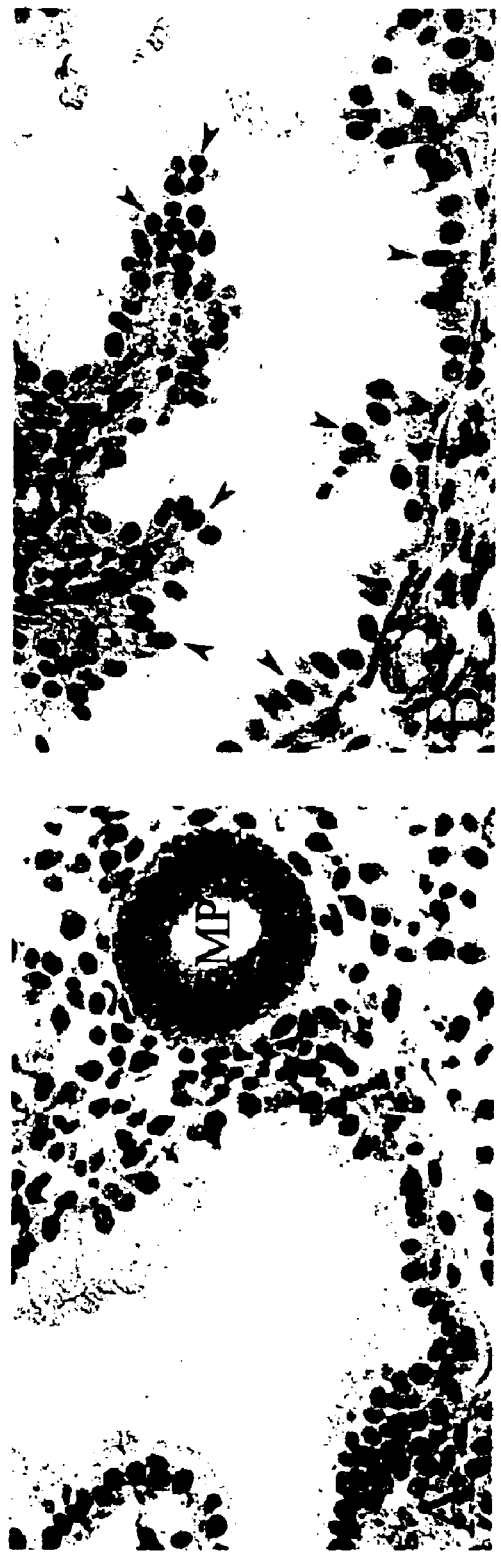
FIGS. 4A and 4B shows immunohistohemical staining for cyclin E in dyssynchronous endometrial biopsies, revealing "differentiation specific expression" (DSE) of cyclin E. DSE is one subset of the general observation of glandular developmental arrest (GDA).

Dyssynchronous biopsies were those in which the dating of the glands and stroma did not consistently correlate throughout the biopsy. The dyssynchronous glands were found to have patterns of cyclin E and p27 expression and sub-cellular localization consistent with their histologically determined date. For example, when immunohistochemically stained for cyclin E, glands which appear to be CD 16–17 within CD 24 stroma had a membrane associated and basal pattern of cytoplasmic staining while glands which appeared to be CD 18–19 had nuclear staining (FIGS. 4A and 4B). We termed this linkage of histologic date with cyclin E and p27 staining "Differentiation Specific Expression" (DSE).

DSE for cyclin E can be seen in the immunohistochemically stained dyssynchronous endometrial biopsies shown in FIGS. 4A and 4B. FIG. 4A shows a biopsy sampled on CD 25 with primarily CD 25 glands and an occasional arrested mid-proliferative (MP) gland whose strong membrane patterned cyclin E cytoplasmic staining is consistent with its histologic dating. This biopsy shown in FIG. 4B was sampled on CD 25, and has primarily CD 25 glands with an occasional arrested CD 18–19 gland, which exhibits strong cyclin E nuclear staining that is typical of CD 19 glands.

In our study, 100% of dyssynchronous glands appeared to be at CD 17–18. The question, however, is whether these glands are truly functioning like glands at these earlier cycle days—whether there is truly an arrest of glandular development—or whether these glands only appear to be at CD 17–18, but in fact are developmentally consistent with the later surrounding stroma. We found that cyclin E and p27 expression was appropriate for the apparent morphologic CD, thus indicating that the cells were behaving as they would at this earlier part of the menstrual cycle. The presence of DSE supports the idea that there is true glandular developmental arrest (GDA) at the earlier phase of development in dyssynchronous glands.

Example 5

According to a preferred protocol two biopsies are evaluated: one on day 15 (defined as two days after LH surge or one day after progesterone treatment begins, or one day after ovulation is determined by ultrasound). The second biopsy on day 24 (defined as 11 days after LH surge, 10 days after progesterone treatment start or 10 days after ovulation). If none of these timing methods are available, than cycle day is determined from first day of last menstrual period (LMP). If only one biopsy can be taken or if only one is acceptable to the patient/doctor, we prefer the day 24 biopsy.

The interpretation of the day 15 versus the day 24 biopsies is different. Below is a table giving the ranges of normal for each of these days:

| Normal Expression of Cyclin E and p27 | | | |
| --- | --- | --- | --- |
| Cycle Day | Cyclin E Cytoplasm | Cyclin E Nuclear | p27 |
| 15 | 50% or more of the glands are positive with 2–3+ staining intensity. Pattern is membrane associated (along inside edges of cells). | No staining | No staining |
| 24 | No staining (up to 5% tolerated to be still normal) | No staining (up to 5% tolerated to be still normal). | 50% or more of the gland nuclei are positive with at least a 1+ staining intensity |

| Normal Expression of MAG and PR in Endometrial Glands | | |
| --- | --- | --- |
| Cycle Days | MAG | PR |
| 5–18 | 10–100% positive glands | 20–100% positive glands |
| 19–25 | No staining (up to 10% tolerated to be still normal). | No staining (no positivity is normal). |

MAG stains the Golgi within the cytoplasm. PR only stains the nuclei.

Abnormals are assessed on a case by case basis. First the stroma is assessed to determine its relationship to the stated clinical cycle day, then the gland developmental day is assessed. If greater than 30% of the glands appear by histology to be delayed by more than two days from the stromal dating than the diagnosis of "glandular-stromal dyssynchrony" is made. Then each marker is assessed in relationship to what it should be at the stated clinical cycle day. Glandular developmental arrest (GDA) for each marker is diagnosed if more than 10% of the glands are at a different (usually delayed) developmental state than the stroma.

Example 6

The cycle day of a biopsy is determined by different criteria depending on the general cycle time. Hendrickson and Kempson's Decision Tree for Endometrial Dating (From Bennington J. L. 1980. Surgical pathology of the uterine corpus. Major Problems Pathology. 12:84), which is incorporated by reference discloses a preferred method of determining the cycle date. The menstrual cycle, by this method, is divided into three phases: proliferative, early secretory and mid to late secretory. Days within the proliferative and early secretory phases are distinguished by glandular features while days within the mid and late secretory phases are distinguished by stromal features.

Specifically, biopsies from day 5 to 14 are dated by the gland architecture, presence of mitotic figures, some characteristics of the stroma (edema appears in the mid-proliferative days of 7–10) and by the fact that the glands do not have any vacuoles. From day 15 onwards, the following are the key criteria for dating:

Gland determined days:
d15: subnuclear vacuoles, <50% of glands
d16: subnuclear vacuoles, >50% of glands; many mitotic figures
d17: uniformly aligned subnuclear vacuoles and nuclei in glands
d18: supranuclear vacuoles in glands, mitotic figures rare
d19: vacuoles infrequent in glands, luminal secretions
d20: maximal glandular luminal secretions, no more vacuoles in glands
Stroma determined days:
d21: beginning of stromal edema
d22: maximal edema in the stroma
d23: spiral arteries of the stroma first prominent
d24: periarterial cuffs of predecidua around spiral arteries of stroma
d25: islands of predecidua in stroma
d26: coalescence of predecidua in stroma
d27: confluent stromal decidualization
d28: breakdown of stroma, beginning of menses Example 7

Each marker has its own special use at different times of the cycle. On day 15 cyclin E tells you that the glands have been adequately stimulated by estrogen (as would progesterone receptor). It is usually positive, but can be negative and then we know we have an estrogen problem (either not enough or a poor response to estrogen). On day 15 p27 should be negative. If it is positive than we know that progesterone stimulation has started too early.

On day 24 cyclin E should be completely negative. Greater than 10% nuclear staining is GDA. The cutoff for cytoplasmic cyclin E is 10%, and in some embodiments 20% or greater, as indicative of GDA in the absence of any nuclear cyclin E staining.

Example 8

During a hyperstimulation cycle, the following testing protocol is performed:
Detect cycE at 2 days after start of P (progesterone)
Detect p27 at 2 days after start of P (progesterone)
Detect cycE at 10 days after start of P (progesterone)
Detect p27 at 10 days after start of P (progesterone)

Example 9

Hormone replacement therapy is discussed in detail in the monograph entitled Individual Hormone Therapy to Promote Better Health and Quality of Life which is posted on the world wide web.

Hormone replacement therapy (HRT) is treatment with hormones, either estrogen alone or in combination with progesterone, to replenish the natural hormones that decrease at menopause. Estrogen replacement therapy (ERT) refers to the use of estrogen alone (called unopposed estrogen). About 12 million women in the United States take prescription estrogen alone and about 8.6 million women are on the combined hormone regimen, according to drug company estimates.

Menopause is the transition between a woman's childbearing years and her non-childbearing years. It is the last stage of a biological process during which the ovaries gradually produce lower levels of sex hormones—estrogen, progesterone, and testosterone. By the time natural menopause is complete (usually between ages 45 and 55) hormone output decreases significantly. In postmenopausal women, estrogen levels are about 1/10 the level of premenopausal women and progesterone is essentially absent. The low levels of estrogen after menopause are produced by the adrenal glands, liver, kidneys, and fat cells. HRT usage approximately doubles the estrogen level of a postmenopausal woman. Therefore, even with HRT, estrogen and progesterone levels of a postmenopausal woman do not reach the level of a premenopausal woman.

Doctors may recommend using estrogen alone or in combination with progestin (natural or synthetic forms of progesterone) to counter some of the possible effects of natural or surgical menopause (removal of ovaries) on a woman's health and quality of life. Symptoms of menopause may include hot flashes, sleeplessness, and vaginal dryness.

Hormones may also be prescribed to prevent some long-term effects such as osteoporosis and coronary heart disease.

Studies have shown that prolonged exposure of the uterus to estrogen without progesterone increases a women's risk of endometrial cancer (cancer of the uterine lining). By adding progestin to the estrogen regimen, the risk of endometrial cancer can be reduced to essentially the same level as non-users. However, some studies have shown increases in endometrial cancer risk with the combined regimens if progestins are used for less than 10 days per month.

Generally, standard hormone replacement therapy for women who have undergone hysterectomy (surgical removal of uterus) is estrogen alone, whereas women who have not undergone this procedure are given the estrogen-progestin combination.

Currently, there are no surveillance techniques that can accurately assess a women's risk to develop endometrial cancer while on HRT. The most commonly used approach is endometrial biopsy and pathologic assessment of an hematoxylin and eosin (H & E) stained slide. Although a number of grading schemes have been developed based on H & E appearances alone, this approach does not assess the state of cellular differentiation of the endometrium. This precludes the use of H & E assessment to evaluate the proliferative potential of a given endometrial biopsy.

We propose using cyclins to assess the true developmental state and proliferative potential of the endometrium. Such an approach will facilitate the surveillance of the endometrium for the appearance of endometrial hyperplasia and cancer during HRT. In addition, cyclin, specifically cyclin E and p27, assessment of an endometrial biopsy can be used to optimize dosages and agents to be used for HRT in the individual patient.

Use of cyclin E and p27 to identify hyperplasia and carcinoma in endometrial biopsy specimens Cyclin E and p27 together can be used to accurately assess the developmental state of the endometrium.

While it might be expected that hyperplasia with atypical endometrial glands represents a precursor to endometrial cancer, evaluation of these glands with cyclin E and p27 can identify glands that are not proliferative in nature and therefore are unlikely to be precursors to endometrial cancer. Conversely, expression of high cyclin E and low p27 in a specimen of atypical hyperplasia would be very concerning and would justify one of the following management courses: 1) altering the regimen of HRT; 2) stopping all HRT; or, in cases of marked endometrial glandular abnormalities, 3) cessation of HRT followed by dilation and curettage, endometrial ablation or hysterectomy.

One clinical trial completed in the 1990s, the Postmenopausal Estrogen/Progestins Intervention (PEPI) trial, looked at changes in HDL, LDL, fibrinogen, blood pressure and serum insulin resulting from estrogen or estrogen/progestin use. The results showed that HDL was increased significantly, LDL and fibrinogen levels were decreased significantly, and blood pressure and serum insulin levels were essentially unaffected.

Over the last 25 years, observational studies (which did not set out to study heart disease and estrogen directly) have suggested a reduction in risk of as much as 25 percent to 50 percent for coronary heart disease in postmenopausal women using HRT. Most of the participants in these studies were healthy women at low risk for CHD, which is the most common cause of death in older women. (In 1997, about 498,000 women died of cardiovascular disease whereas about 42,000 women died of breast cancer, according to the latest figures from the National Center for Health Statistics.)

A recent, randomized, clinical trial, the Heart and Estrogen/Progestin Replacement Study (HERS), among women who had a prior history of heart disease, showed no overall reduction in CHD. The HERS study was the first randomized, controlled trial to look at HRT and heart disease directly. It stands in contrast to the many observational studies suggesting that HRT is protective for CHD.

The majority of studies on the effect of HRT on cardiovascular disease and mortality to date have been conducted using estrogens alone; only a few have investigated the effects of combined progestogen and estrogen therapy. One of those, the Nurse's Health Study, which followed 59,337 women for 16 years, evaluated the effects of estrogen vs. the estrogen-progestogen combination on CHD. This study found that women taking the estrogen-progestogen combination had a greater reduction in risk of a major coronary event compared with women who used estrogen alone. Risk was lower in both groups of users, compared to non-users.

Postmenopausal osteoporosis is characterized by decreased bone mass, deterioration of bone tissue, and high bone fragility, making bone fractures of great concern. Estrogen deficiency is the most common risk factor for osteoporosis in women.

Estrogen, with and without progestin, has been seen to be a protective and effective against osteoporosis. However, some studies have shown that the beneficial effects of short-term therapy are not permanent; short-term use (three to five years) of estrogen to relieve symptoms of menopause did very little to prevent fractures from osteoporosis in women when they reached age 75 to 80 years of age. Some literature suggests that hormone use started later in life offers bone-conserving benefits nearly equal to those who began therapy earlier.

Over the last 25 years, numerous studies have examined the possible relationship between HRT and breast cancer. Some of the studies showed an increased risk while others did not.

A recent re-analysis of over 90 percent of breast cancer studies throughout the world showed an increased risk in breast cancer for women who used HRT for five years or longer. (The risk was not only seen in current users, but also in women who stopped therapy sometime in the previous four years. No risk was seen in women who had stopped the therapy for more than four years.) Most of the women included in the re-analysis were on estrogen alone.

Recent studies have shown the risk of breast cancer to be greater among women using combination estrogen/progestin, compared to estrogen alone. Both groups of hormone users had a higher risk of breast cancer than non-users. The risk increased with longer duration of use, and returned to the risk of non-users five or more after use was stopped.

Studies have shown a slightly lower total mortality rate among postmenopausal women using HRT. On average, the mortality among users of postmenopausal hormones has been lower than that of women who do not use hormones, but the survival benefit has been seen to diminish with longer duration of use. It is not clear whether this reduction in mortality is entirely due to the biologic effect from the use of hormones or whether the women who use hormones are healthier.

There have been some reports that the use of HRT may improve a woman's mood and psychological well-being, though evidence for the use of estrogen as a therapeutic agent for symptoms such as irritability and depression are inconclusive. In addition, one study showed that estrogen use in postmenopausal women may delay the onset and decrease the risk of Alzheimer's disease.

Women with certain pre-existing heart conditions are usually advised not to take HRT. These conditions include a history of blood clots (venous thromboembolisms) and recent heart attacks. Several studies have shown the risk of blood clots among women currently using HRT to be two to three times higher than non-HRT users. Increased cases of lung clots (pulmonary embolisms) and inflammation of veins (thrombophlebitis) have also been reported with HRT use.

Another reported risk associated with HRT use is the development of gallstones.

Only a small amount of research has been done to look at the risks associated with HRT for women who have a history of endometrial cancer. While there is no current evidence that HRT adversely influences survival and/or recurrence of the disease in these women, there is no evidence that the potential benefits outweigh the risks. An ongoing study (ERT Study) sponsored by the National Cancer Institute, is designed to resolve the debate over whether women who have had early stage cancer of the uterus, or endometrial cancer, can safely take estrogen replacement therapy.

The safety of replacing women's estrogens after breast cancer is unknown. At least one trial is underway to address this issue, but the results will not be available for several years.

Most women will eventually need to make decisions about whether to take HRT and, if for how long. Although hormone replacement therapy can have beneficial effects for many women, there are several health concerns associated with it, and all women do not feel that HRT is a good choice for them.

There are several non-hormonal measures that may prevent osteoporosis and cardiovascular disease, including avoidance of smoking, regular exercise, and a healthy diet. Several studies have shown a decrease in the incidence of osteoporosis and cardiovascular disease with modifications in diet and lifestyle. In addition, non-hormonal prescription drugs are available to lower blood cholesterol and slow bone loss, such as the statins to lower blood cholesterol. Calcium and vitamin D supplements are recommended by some health professionals as a means of preventing osteoporosis.

Many women find relief from short-term menopause-related changes with non-prescription remedies, such as estrogen-containing foods (soy products, whole-grain cereal, seeds, fruits, vegetables) and creams, certain herbs such as black cohosh, and vitamin E and vitamin B complexes. Researchers are studying the safety and efficacy of these therapies. Local therapy, such as estrogen-cream therapy, is available for vaginal dryness and urinary bladder conditions. The estrogen dose of this therapy is lower than HRT.

Short-term menopause-related changes may resolve on their own and frequently require no therapy at all.

Finally, improved methodologies to optimize HRT dosing and combinations—as well as improved strategies for accurate endometrial surveillance—will enhance the efficacy of HRT and decrease an important risk factor in its long term use. This will translate into increased numbers of women who can safely and effectively take HRT, thus improving the quality of life for many aging women.

Example 10

A preferred embodiment of the invention provides an Endometrial Function Test (EFT) which is a panel of antibody tests performed on samples obtained from cycle day 15 (preferably day 14, 15 or 16) and cycle day 24 (preferably day 23, 24 or 25) (as determined by stated clinical, cycle date by LH surge, cycle day by progesterone administration date (P=14) and by histological dating).

The antibody tests include 1) A, 2) B, and 3) blood groups, 4) progesterone receptor, 5) MAG C30, 6) Cyclin E and 7) p27. The MAG C30 analysis is only applicable for those patients who are A blood group positive. The analysis and diagnosis therefrom is based upon expression positivity and localization is as described herein. The directions for obtaining samples is as follows.

Ideally take biopsies on cycle day 15 (LH+2, or second day of P for mock cycles) and cycle day 24 (LH+11, or day 10 of P for mock cycles). If only one biopsy is possible, cycle day 24 biopsy is preferable. Note, we assume the urine LH surge occurs on cycle day 13, ovulation and the first day of P are defined as day 14.

Perform standard Pipelle biopsy (pull plunger, rotate Pipelle as you withdraw from uterus).

Cut tip of Pipelle off before ejecting tissue into fixative

Place in standard 10% Neutral Buffered Formalin (NBF) in soft plastic (polypropylene) tube with tight cap. Biopsies should be sent the same day as the procedure, except on Fridays and weekends, in which case the biopsy should be refrigerated and sent the following Monday.

Please include all requested patient information with specimens by filling out the Request for Endometrial Assessment and Consultation form.

Send only via Overnight (overseas clinicians can use standard airmail).

Optimal days of biopsy and shipping are Monday through Thursday to avoid weekend receipt (the specimen may be returned to you if received on Saturday).

Unstained Slides Protocol for Developmental Marker Analysis

Have previously fixed and embedded endometrial biopsy processed in your histology laboratory to generate 12 unstained slides on coated slides made for immunohistochemistry. Specifically request lab not to heat slides.

Place slides into strong plastic slide holding containers, tape closed.

Standard mail is sufficient for these recuts.

Example 11

A discussion of ovulation inducing drugs is included in the guide "Ovulations Drugs, A Guide for Patients" which is incorporated by reference and which is published by the American Society for Reproductive Medicine (2000), 1209 Montgomery Highway, Birmingham Ala. 35216-9822.

References

The references cited herein are intended to be incorporated by reference. They refer to subject matter disclosed in the background of the invention.

1. Mosher, W. D. 1987. Infertility: why business is booming. *Am Demograph.* 9:42–43.
2. Society for assisted reproductive technology 1997 national report. 1999. Centers for Disease Control, Atlanta, Ga.
3. Treolar, A. E., Boynton, R. E., Behn, B. G., and Brown, B. W. 1967. Variation of the human menstrual cycle through the reproductive life. *Internat J Feril.* 12:77–126.
4. Navot, D., Scott, R. T., Droesch, K., Veeck, L. L., Liu, H-C., et al. 1991. The window of embryo transfer and the efficiency of human conception in vitro. *Fertil Steril.* 55:114.
5. Bergh, P. A. and Navot, D. 1992. The impact of embryonic development and endometrial maturity on the timing of implantation. *Fertil Steril.* 58:537–42.
6. Noyes, R. W., A. T. Hertig, and Rock, J. 1950. Dating the endometrial biopsy. *Fertil Steril.* 1:3–25.
7. Noyes, R. W. 1956. Uniformity of secretory endometrium: study of multiple sections from 100 uteri removed at operation. *Fertil Steril.* 7:103.
8. Johannisson, E., Landgren, B-M., Rohr, H. P. and Diczfalusy, E. 1987. Endometrial histology and peripheral hormone levels in women with regular menstrual cycle. *Fertil Steril.* 48:401–408.
9. Noyes, R. W. and Haman, J. O. 1953. Accuracy of endometrial dating. *Fertil Steril.* 4:504.
10. Scott, R. T., Snyder, R. R., Strickland, D. M., Tyburski, C. C., Bagnall, J. A., et al. 1988. The effect of interobserver variation in dating endometrial histology on the diagnosis of luteal phase defects. *Fertil Steril.* 50: 888–892.
11. Yen, S. S. C., Jaffe, R. B., and Barbieri, R. L. 1999. Reproductive endocrinology: physiology, pathophysiology, and clinical management. W. B. Saunders Company.
12. Gibson, M., Badger, G. J. Byrn, F., Lee, K. R., Korson, R., et al. 1991. Error in histologic dating of secretory endometrium: variance component analysis. *Fertil Steril.* 56:242–247.
13. Li, T-C., Dockery, P., Rogers, A. W., and Cook, I. D. 1989. How precise is histologic dating of endometrium using the standard dating criteria? *Fertil Steril.* 51:759.
14. Smith, S., Hosid, S. and Scott, L. 1995. Endometrial biopsy dating: interobserver variation and its impact on clinical practice. *J Repro Med.* 40: 1–3.

15. Hendrickson, M. R., Kempson, R. L. 1980. Surgical pathology of the uterine corpus. *Major Problems Pathololgy*. 12:36–98.
16. Mishell, D. R., Davajan, V., and Lobo, R. A. 1991. Infertility, contraception and reproductive endocrinology. Blackwell Scientific Publications.
17. Blasco, L. 1994. Dyssynchrony in the maturation of endometrial glands and stroma. *Fertil Steril.* 61:596–7.
18. Gurpide, E., and Bulletti, C. 1991. Introduction: research on the human endometrium. *Ann New York Aca Sci.* 622:1–5.
19. Schatz, F., Hausknecht, V., Gordon, R. E., et al. 1991. Studies on human endometrial cells in primary culture. *Ann New York Acta Sci.* 622:1–5
20. Satyaswaroop, P. G., Bressler, R. S., de la Penna, M. M., and Gurpide, E. 1979. Isolation and culture of human endometrial glands. *J Clin Endocrinol Metab.* 48:639–641.
21. Li, T-C., Rogers, A. W., Dockery, P., Lenton, E. A., and Cooke, I.D. 1988. A new method of histologic dating of human endometrium in the luteal phase. *Fertil Steril.* 50:52–60.
22. Johannisson, E., Parker, R. A., Landgren, B-M., and Diczfalusy, E. 1982. Morphometric analysis of the human endometrium in relation to peripheral hormone levels. *Fertil Steril.* 38:564–571.
23. Castelbaum, A. J., Wheeler, J., Coutifaris, C. et al. 1994. Timing of the endometrial biopsy may be critical for the accurate diagnosis of luteal phase deficiency. *Fertil Steril.* 61:443–7.
24. Dockery, T. C., Rogers, A. W., and Cooke, I. D. 1990. A quantitative study of endometrial development in the luteal phase: comparison between women with unexplained infertility and normal fertility. *Brit J Ob Gyn.* 97:576–582.
25. Dockery, P, Pritchard, K., Warren, M. A., Li, T. C., and Cooke, I. D. 1996. Changes in nuclear morphology in the human endometrial glandular epithelium in women with unexplained infertility. *Hum Repro.* 11:2251–2256.
26. Lessey, B. A., Damjanovich, L., Coutifaris, C., et al. 1992. Integrin adhesion molecules in the human endometrium. correlation with the normal and abnormal menstrual cycle. *J Clin Invest.* 90:188–195.
27. Taylor, H. S., Arici, A., Olive, D., and Igarashi, P. 1998. HOXA10 is expressed in response to sex steroids at the time of implantation in the human endometrium. *J Clin Invest.* 101:1379–1384.
28. Kliman, H. J., Feinberg, R. F., Schwartz, L. B., Feinman, M. A., Lavi, E., et al. 1995. A mucin-link glycoprotein identified by MAG (mouse ascites golgi) antibodies. *Am J Pathol.* 146:166–181.
29. Lessey, B. A., Castelbaum, A. J., Sawin, S. W., Buck, C. A., Schinnar, R., et al. 1994. Aberrant integrin expression in the endometrium of women with endometriosis. *J Clin Endocrinol Metab.* 79:643–649.
30. Meyer, W. R., Castelbaum, A. J., Somkuti, S., Sagoskin, A. W., Doyle, M., et al. 1997. Hydrosalpinges adversely affect markers of endometrial receptivity. *Human Reproduction.* 12:1393–1398.
31. Lessey, B. A., Castelbaum, A. J., Sawin, S. W., and Sun, J. 1995. Integrins as markers of uterine receptivity in women with primary unexplained infertility. *Fertil Steril.* 63:535–542.
32. Creus, M., Balasch, J., Ordi, J. Fabregues, F., Casamitjana, R., et al. 1998. Integrin expression in normal and out-of-phase endometria. *Hum Reprod.* 13:3460–3468.
33. Enders, A. C., and Schlafke, S. 1974. Surface coat of the mouse blastocyst and the uterus during the preimplantation period. *Anat Rec.* 181:31–46.
34. Hewitt, K., Beer, A. E., and Grinnell, F. 1979. Disappearance of anionic sites from the surface of the rat endometrial epithelium at the time of blastocyst implantation. *Biol Reprod.* 21:691–707.
35. Anderson, T. L., Olsen, G. E., and Hoffman L. H. 1986. Stage specific alterations in the apical membrane glycoproteins on endometrial epithelial cells related to implantation in rabbits. *Biol Reprod.* 34:701–720.
36. Kliman H J, L I Barmat, and F F Wang. 1997. MAG mucin expression abnormalities in natural cycle biopsies predict subsequent IVF failure. Society for Reproductive Medicine, Cincinnati. (Abstr.)
37. Kliman, H. J., Arruda, J. S., Feinberg, R. F., and Keefe, D. L. 1998. Absence of biochemical or morphologic markers of endometrial glandular development in a mock cycle predicts pregnancy failure in a subsequent donor oocyte transfer cycle. American Society for Reproductive Medicine, San Francisco. (Abstr.)
38. Morgan, D. O. 1997. Cyclin-dependent kinases: engines, clocks, and microprocessors. *Annu Rev Cell Dev Biol.* 13:261–91.
39. Hamel, P. A., and Hanley-Hyde, J. 1997. G1 cyclins and control of the cell division cycle in normal and transformed cells. *Cancer Investigation.* 15(2):143–152.
40. Sheaff, R. J., Groudine, M., Gordon, M., Roberts, J. M., and Clurman, B. E. 1997. Cyclin E-CDK2 is a regulator of p27. *Genes Devel.* 11:1464–1478.
41. Kwon, T. K., and Nordin, A. A. 1997. Overexpression of cyclin E and cyclin-dependent kinase inhibitors (p27 Kip1): Effect on Cell Cycle Regulation in HeLa Cells. *Biochem and Biophys Research Comm.* 238:534–538.
42. Bamberger, A-M., Riethdorf, L., Milde-Langosch, K., Bamberger, C. M., Thuneke, I., et al. 1999. Strongly reduced expression of the cell cycle inhibitor p27 in endometrial neoplasia. *Virchows Arch.* 434:423–28.
43. Lloyd, R. V., Erickson, L. A., Jin, L., Kulig, E., Qian, X., et al. 1999. p27Kip1: A multifunctional cyclin-dependent kinase inhibitor with prognostic significance in human cancers. *Am J Pathol.* 154:313–323.
44. Reynisdottir, I., and Massague, J. 1997. The subcellular locations of p15ink4b and p27Kip1 coordinate their inhibitory interactions with CDK4 and CDK2. *Genes Dev.* 11:492–503.
45. Orend, G., Hunter, T., and Ruoslahti, E. 1998. Cytoplasmic displacement of dyclin E-CDK2 inhibitors p21Cip1 and p27Kip1 in anchorage independent cells. *Oncogene.* 16:2575–2583.
46. Singh, S. P., Lipman, J., Goldman, H., Ellis, F. H., Aizenman, L., et al. 1998. Loss or altered subcellular localization of p27 in Barrett's associated adenocarcinoma. *Cancer Res.* 58:1730–1735.
47. Soucek, T., Yeung, R. S., and Hengstschlager, M. 1998. Inactivation of the cyclin-dependent kinase inhibitor p27 upon loss of the tuberous sclerosis complex gene-2. *Proc Natl Acad Sci.* 95:15653–15658.
48. Shiozawa, T., Li, S-f., Nakayama, K., Nikaido, T., and Fujii, S. 1996. Relationship between the expression of cyclins/cyclin-dependent kinases and sex steroid receptors/Ki67 in normal human endometrial glands and stroma during the menstrual cycle. *Mol Hum Reprod.* 2:745–52.
49. Shiozawa, T., Nikaido, T., Nakayama, K., Lu, X., and Fujii, S. 1998. Involvement of cyclin-dependent kinase inhibitors p27Kip1 in growth inhibition of endometrium in the secretory phase and of hyperplastic endometrium treated with progesterone. *Mol. Hum Reprod.* 4:899–905.
50. Musgrove, E. A., and Sutherland, R. L. 1994. Cell cycle control by steroid hormones. *Sem Cancer Biol.* 5:381–389.
51. Musgrove, E. A., Swarbrick, A., Lee, C. S. L., Cornish, A. L., and Sutherland, R. L. 1998. Mechanisms of cyclin-dependent kinase inactivation by progestins. *Mol. Cell Biol.* 1812–1825.
52. Tavani A, La Vecchia C. The adverse effects of hormone replacement therapy. Drugs Aging 1999;14:347–57.
53. Pike M C, Peters R K, Cozen W, et al. Estrogen-progestin replacement therapy and endometrial cancer. J Natl Cancer Inst 1997;89:1110–1116.
54. Beresford S, Weiss N, Voigt L, et al. Risk of endometrial cancer in relation to use of oestrogen combined with cyclic progestagen therapy in postmenopausal women. Lancet 1997;349:458–461.
55. Kurman R J, Norris H J. Endometrial hyperplasia and related cellular changes. In: Blaustein's pathology of the female genital tract. Ed: Kurman R J. Springer-Verlag, New York, pp 411–437.
56. Bush T L. Evidence for primary and secondary prevention of coronary artery disease in women taking oestrogen replacement therapy. Eur Heart J 1996;17:9–14.
57. Rosano G M, and Painina G. Cardiovascular pharmacology of hormone replacement therapy. Drugs Aging 1999;15:219–234.
58. Rossouw J E. Hormone replacement therapy and cardiovascular disease. Curr Opin Lipidol 1999;10:429–34.
59 Grodstein F, Stampfer M J, Colditz G A, et al. Postmenopausal hormone therapy and mortality. N Engl J Med 1997; 336(25):1769–1775.
60 Reid I R. Pharmacological management of osteoporosis in postmenopausal women: a comparative review. Drugs Aging 1999; 15:349–63.
61. Rosenberg S, Vandromme J, Ayata N B, et al. Osteoporosis Management. Int J Fertil Womens Med 1999;44:241–9.
62. Schneiser D L, Barrett-Connor E L, Morton D J. Timing of postmenopausal estrogen for optimal bone mineral density: the Rancho Bernardo Study. JAMA 1997; 277:543–547.
63. Collaborative Group on Hormonal Factors in Breast Cancer. Breast cancer and hormone replacement therapy. Lancet 1997;350: 1047–1059.
64. Ross R K, Paganini-Hill A, Wan P C, et al. Effective hormone replacement therapy on breast cancer risk: estrogen versus estrogen plus progestin. J Natl Cancer Inst 2000;92:328–332.
65. Schairer C, Lubin J, Troisi R, et al. Menopausal estrogen and estrogen-progestin replacement therapy and breast cancer risk. JAMA 2000; 283:485–491.
66. Scharbo-Dehaan M. Hormone replacement therapy. Nurse Pract. 1996; 21 (12 Pt 2):1-13.
67. Tang M X, Jacobs D, Stem Y, et al. Effect of oestrogen during menopause on risk and age at onset of Alzheimer's disease. Lancet 1996; 348(9025):429–32.
69. Castellsague J, Perez Gutthann S, Garcia Rodriguez L A. Recent epidemiological studies of the association between hormone replacement therapy and venous thromboembolism. A review. Drug Safety 1998; 18:117–23.
70. Kakar F, Weiss N S, Strite S A. Noncontraceptive estrogen use and risk of gallstone disease in women. Am J Public Health 1988; 78:564.
71. Burger C W, van Leeuwen F E, Scheele F, Kenemans P. Hormone replacement therapy in women treated for gynaecological malignancy. Maturitas 1999; 32:69–76.
72. Seifert M, Galid A, Kubista E. Estrogen replacement therapy in women with a history of breast cancer. Maturitas 1999;32:63–8.
73. Vassilopoulou-Selin R, Asmar L, Hortobagyi G N, et al. Estrogen replacement therapy after localized breast cancer: clinical outcome of 319 women followed prospectively. J Clin Oncol 1999;5:1482–1487.
74. Vassilopoulou-Selin R, Theriault R L. Randomized prospective trial of estrogen-replacement therapy in women with a history of breast cancer. Monog Natl Cancer Inst 1994;6:153–159.
76. Pedersen T R. Statin trials and goals of cholesterol-lowering therapy after AMI. Am Heart J 1999; 138(2 Pt 2):177–82.
77. Keller C, Fullerton J, Mobley C. Supplemental and complementary alternatives to hormone replacement therapy. Amer Acac Nurse Pract 1999;11: 187–98.
78. Design of the women's health initiative clinical trial and observational study. The women's health initiative study group. Control Clin Trials 1998; 19:61–109.

We claim:

1. A method of diagnosing an abnormality in endometrial glandular development in a woman comprising the step of:
detecting expression of cyclin E in the nuclei and/or the cytoplasm of endometrial gland cells in an endometrial tissue sample from on or after day 20 of an idealized 28 day menstrual cycle from a woman;
wherein
expression of cyclin E in the nuclei of greater than 5% of the gland cells indicates endometrial glandular developmental arrest, and/or
expression of cyclin E of greater than 1+ staining intensity in the cytoplasm of greater than 10% of the gland cells indicates endometrial glandular developmental arrest.

2. The method of claim 1 wherein the expression of cyclin E is detected by an immunohistochemisty assay.

3. The method of claim 1 wherein the cycle day is determined by examining the stroma cells in the sample.

4. The method of claim 1 wherein expression of cyclin E is detected in the nuclei of greater than 10% of the gland cells in the sample is indicative of endometrial glandular developmental arrest.

5. The method of claim 1 wherein the cycle day is day 24 of an idealized 28 day menstrual cycle.

6. The method of claim 1 further comprising the step of detecting the expression of p27 in the nuclei of gland cells in a serial section of the sample.

7. The method of claim 1 further comprising the step of detecting the expression of progesterone receptor in the gland cells in a serial section of the sample.

8. The method of claim 1 further comprising the step of detecting the expression mouse ascites golgi mucin MAG in the gland cells in a serial section of the sample.

9. The method of claim 1 further comprising the steps of detecting the expression of p27 in the nuclei of gland cells in a serial section of the sample and either detecting the expression of progesterone receptor in the gland cells in a serial section of the sample or detecting the expression of MAG in the gland cells in a serial section of the sample or both.

10. The method of claim 1 further comprising the step of detecting expression of cyclin E in the nuclei and/or the cytoplasm of endometrial gland cells in an endometrial tissue sample from on or before day 18 of an idealized 28 day menstrual cycle from the woman.

11. The method of claim 1 further comprising the step of detecting expression of cyclin E in the nuclei and/or the cytoplasm of endometrial gland cells in an endometrial tissue sample from day 15 an idealized 28 day menstrual cycle from the woman.

12. The method of claim 1 further comprising the step of detecting expression of p27 in the nuclei of endometrial gland cells in an endometrial tissue sample from on or before day 18 of an idealized 28 day menstrual cycle from the woman.

13. The method of claim 1 further comprising the step of detecting expression of p27 in the nuclei of endometrial gland cells in an endometrial tissue sample from before day 17 of an idealized 28 day menstrual cycle from the woman wherein expression of p27 is indicative of accelerated endometrial glandular development.

14. The method of claim 1 further comprising the step of detecting expression of progesterone receptor in the gland cells in an endometrial tissue sample from before day 18 of an idealized 28 day menstrual cycle from the woman.

15. The method of claim 1 further comprising the step of detecting the expression of MAG in the gland cells in an endometrial tissue sample from on or before day 18 of an idealized 28 day menstrual cycle from the woman.

16. The method of claim 1 further comprising at least two of the following steps of:
   a) detecting the expression of cyclin E in the nuclei and/or cytoplasm of the gland cells in an endometrial tissue sample from on or before day 18 of an idealized 28 day menstrual cycle from the woman;
   b) detecting the expression of p27 in the nuclei of gland cells in an endometrial tissue sample from on or before day 18 of an idealized 28 day menstrual cycle from the woman;
   c) detecting expression of progesterone receptor in gland cells in an endometrial tissue sample on or before day 18 of an idealized 28 day menstrual cycle from the woman;
   d) detecting the expression of MAG in the gland cells in an endometrial tissue sample from on or before day 18 of an idealized 28 day menstrual cycle from the woman;
wherein said two or more steps are performed on serial sections of the sample.

17. A method of predicting abnormal endometrial glandular development comprising the steps of:
   detecting the level of p27 in the nuclei of cells in a sample of endometrial tissue from day 10–18 of an idealized 28 day menstrual cycle from a woman and
   comparing the level of expression with an expected level of expression;
   wherein detection of elevated levels of p27 in the sample is predictive that the woman will be diagnosed with endometrial glandular developmental arrest.

18. The method of claim 17 wherein the expression of p27 is detected by an immunohistochemisty assay.

19. The method of claim 17 wherein the cycle day is determined by examining the stroma and gland cells in the sample.

20. The method of claim 17 wherein the cycle day is day 15 of a idealized 28 day menstrual cycle.

21. The method of claim 17 further comprising the step of detecting the expression of cyclin E in the nuclei and/or cytoplasm of gland cells in a serial section of the sample.

22. The method of claim 17 further comprising the step of detecting the expression of progesterone receptor in the gland cells in a serial section of the sample.

23. The method of claim 17 further comprising the step of detecting the expression MAG in the gland cells in a serial section of the sample.

24. The method of claim 17 further comprising at least two of the following steps of:
   a) detecting the expression of cyclin E in the nuclei and/or cytoplasm of the gland cells in an endometrial tissue sample from on or before day 18 of an idealized 28 day menstrual cycle from the woman;
   b) detecting expression of progesterone receptor in gland cells in an endometrial tissue sample from on or before day 18 of an idealized 28 day menstrual cycle from the woman;
   c) detecting the expression of MAG in the gland cells in an endometrial tissue sample on or before day 18 of an idealized 28 day menstrual cycle from the woman;
wherein said two or more steps are performed on serial sections of the sample.

25. A method of diagnosing an abnormality in endometrial glandular development in a woman suspected of being infertile comprising the step of:
   detecting expression of cyclin E in the nuclei and/or the cytoplasm of endometrial gland cells in an endometrial tissue sample from on or after day 20 of an idealized 28 day menstrual cycle from said woman;
   wherein
   expression of cyclin E in the nuclei of greater than 5% of the gland cells indicates endometrial glandular developmental arrest, and/or
   expression of cyclin E of greater than 1+ staining intensity in the cytoplasm of greater than 10% of the gland cells indicates endometrial glandular developmental arrest.

26. The method of claim 25 wherein the expression of cyclin E is detected by an immunohistochemisty assay.

27. The method of claim 25 wherein the cycle day is determined by examining the stroma cells in the sample.

28. The method of claim 25 wherein expression of cyclin E is detected in the nuclei of greater than 10% of the gland cells in the sample is indicative of endometrial glandular developmental arrest.

29. The method of claim 25 wherein the cycle day is day 24 of an idealized 28 day menstrual cycle.

30. The method of claim 25 further comprising the step of detecting the expression of p27 in the nuclei of gland cells in a serial section of the sample.

31. The method of claim 25 further comprising the step of detecting the expression of progesterone receptor in the gland cells in a serial section of the sample.

32. The method of claim 25 further comprising the step of detecting the expression mouse ascites golgi mucin MAG in the gland cells in a serial section of the sample.

33. The method of claim 25 further comprising the steps of detecting the expression of p27 in the nuclei of gland cells in a serial section of the sample and either detecting the expression of progesterone receptor in the gland cells in a serial section of the sample or detecting the expression of MAG in the gland cells in a serial section of the sample or both.

34. The method of claim 25 further comprising the step of detecting expression of cyclin E in the nuclei and/or the cytoplasm of endometrial gland cells in an endometrial tissue sample from on or before day 18 of an idealized 28 day menstrual cycle from the woman.

35. The method of claim 25 further comprising the step of detecting expression of cyclin E in the nuclei and/or the cytoplasm of endometrial gland cells in an endometrial tissue sample from day 15 an idealized 28 day menstrual cycle from the woman.

36. The method of claim 25 further comprising the step of detecting expression of p27 in the nuclei of endometrial gland cells in an endometrial tissue sample from on or before day 18 of an idealized 28 day menstrual cycle from the woman.

37. The method of claim 25 further comprising the step of detecting expression of p27 in the nuclei of endometrial gland cells in an endometrial tissue sample from before day 17 of an idealized 28 day menstrual cycle from the woman wherein expression of p27 is indicative of accelerated endometrial glandular development.

38. The method of claim 25 further comprising the step of detecting expression of progesterone receptor in the gland cells in an endometrial tissue sample from before day 18 of an idealized 28 day menstrual cycle from the woman.

39. The method of claim 25 further comprising the step of detecting the expression of MAG in the gland cells in an endometrial tissue sample from on or before day 18 of an idealized 28 day menstrual cycle from the woman.

40. The method of claim 25 further comprising at least two of the following steps of:
   a) detecting the expression of cyclin E in the nuclei and/or cytoplasm of the gland cells in an endometrial tissue sample from on or before day 18 of a an idealized 28 day menstrual cycle from the woman;
   b) detecting the expression of p27 in the nuclei of gland cells in an endometrial tissue sample from on or before day 18 of an idealized 28 day menstrual cycle from the woman;
   c) detecting expression of progesterone receptor in gland cells in an endometrial tissue sample on or before day 18 of an idealized 28 day menstrual cycle from the woman;
   d) detecting the expression of MAG in the gland cells in an endometrial tissue sample from on or before day 18 of an idealized 28 day menstrual cycle from the woman;
wherein said two or more steps are performed on serial sections of the sample.

41. A method of claim 25 wherein said woman is undergoing a hormonal protocol to produce a mock cycle.

42. A method of claim 1 wherein said woman is undergoing a hormonal protocol to produce a mock cycle.

43. A method of claim 17 wherein said woman is undergoing a hormonal protocol to produce a mock cycle.

44. The method of claim 41 wherein the expression of cyclin E is detected by an immunohistochemisty assay.

45. The method of claim 41 wherein the cycle day is determined by examining the stroma cells in the sample.

46. The method of claim 41 wherein expression of cyclin E is detected in the nuclei of greater than 10% of the gland cells in the sample is indicative of endometrial glandular developmental arrest.

47. The method of claim 41 wherein the cycle day is day 24 of an idealized 28 day menstrual cycle.

48. The method of claim 41 further comprising the step of detecting the expression of p27 in the nuclei of gland cells in a serial section of the sample.

49. The method of claim 41 further comprising the step of detecting the expression of progesterone receptor in the gland cells in a serial section of the sample.

50. The method of claim 41 further comprising the step of detecting the expression mouse ascites golgi mucin MAG in the gland cells in a serial section of the sample.

51. The method of claim 41 further comprising the step of detecting the expression of p27 in the nuclei of gland cells in a serial section of the sample and either detecting the expression of progesterone receptor in the gland cells in a serial section of the sample or detecting the expression of MAG in the gland cells in a serial section of the sample or both.

52. The method of claim 41 further comprising the step of detecting expression of cyclin E in the nuclei and/or the cytoplasm of endometrial gland cells in an endometrial tissue sample from on or before day 18 of an idealized 28 day menstrual cycle from the woman.

53. The method of claim 41 further comprising the step of detecting expression of cyclin E in the nuclei and/or the cytoplasm of endometrial gland cells in an endometrial tissue sample from day 15 an idealized 28 day menstrual cycle from the woman.

54. The method of claim 41 further comprising the step of detecting expression of p27 in the nuclei of endometrial gland cells in an endometrial tissue sample from on or before day 18 of an idealized 28 day menstrual cycle from the woman.

55. The method of claim 41 further comprising the step of detecting expression of p27 in the nuclei of endometrial gland cells in an endometrial tissue sample from before day 17 of an idealized 28 day menstrual cycle from the woman wherein expression of p27 is indicative of accelerated endometrial glandular development.

56. The method of claim 41 further comprising the step of detecting expression of progesterone receptor in the gland cells in an endometrial tissue sample from before day 18 of an idealized 28 day menstrual cycle from the woman.

57. The method of claim 41 further comprising the step of detecting the expression of MAG in the gland cells in an endometrial tissue sample from on or before day 18 of an idealized 28 day menstrual cycle from the woman.

58. The method of claim 41 further comprising at least two of the following steps of:
   a. detecting the expression of cyclin E in the nuclei and/or cytoplasm of the gland cells in an endometrial tissue sample from on or before day 18 of an idealized 28 day menstrual cycle from the woman;
   b. detecting the expression of p27 in the nuclei of gland cells in an endometrial tissue sample from on or before day 18 of an idealized 28 day menstrual cycle from the woman;
   c. detecting expression of progesterone receptor in gland cells in an endometrial tissue sample on or before day 18 of an idealized 28 day menstrual cycle from the woman;
   d. detecting the expression of MAG in the gland cells in an endometrial tissue sample from on or before day 18 of an idealized 28 day menstrual cycle from the woman;
wherein said two or more steps are performed on serial sections of the sample.

59. A method of predicting abnormal endometrial glandular development in a woman suspected of being infertile comprising the steps of:
   detecting the level of p27 in the nuclei of cells in a sample of endometrial tissue from day 10–18 of an idealized 28 day menstrual cycle from said woman, and comparing the level of expression with an expected level of expression;
   wherein detection of elevated levels of p27 in the sample is predictive that the woman will be diagnosed with endometrial glandular development arrest.

60. The method of claim 59 wherein the expression of p27 is detected by an immunohistochemisty assay.

61. The method of claim 59 wherein the cycle day is determined by examining the stroma, and gland cells in the sample.

62. The method of claim 59 wherein the cycle day is day 15 of a an idealized 28 day menstrual cycle.

63. The method of claim 59 further comprising the step of detecting the expression of cyclin E in the nuclei and/or cytoplasm of gland cells in a serial section of the sample.

64. The method of claim 59 further comprising the step of detecting the expression of progesterone receptor in the gland cells in a serial section of the sample.

65. The method of claim 59 further comprising the step of detecting the expression MAG in the gland cells in a serial section of the sample.

66. The method of further comprising at least two of the following steps of:
   a) detecting the expression of cyclin E in the nuclei and/or cytoplasm of the gland cells in an endometrial tissue sample from on or before day 18 of an idealized 28 day menstrual cycle from the woman;
   b) detecting expression of progesterone receptor in gland cells in an endometrial tissue sample from on or before day 18 of an idealized 28 day menstrual cycle from the woman;
   c) detecting the expression of MAG in the gland cells in an endometrial tissue sample on or before day 18 of an idealized 28 day menstrual cycle from the woman;
wherein said two or more steps are performed on serial sections of the sample.

67. A method of claim 59 wherein said woman is undergoing a hormonal protocol to produce a mock trial.

68. The method of claim 67 wherein the expression of p27 is detected by an immunohistochemisty assay.

69. The method of claim 67 wherein the cycle day is determined by examining the stroma, and gland cells in the sample.

70. The method of claim 67 wherein the cycle day is day 15 of an idealized 28 day menstrual cycle.

71. The method of claim 67 further comprising the step of detecting the expression of cyclin E in the nuclei and/or cytoplasm of gland cells in a serial section of the sample.

72. The method of claim 67 further comprising the step of detecting the expression of progesterone receptor in the gland cells in a serial section of the sample.

73. The method of claim 67 further comprising the step of detecting the expression MAG in the gland cells in a serial section of the sample.

74. The method of claim 67 further comprising at least two of the following steps of:
   a) detecting the expression of cyclin E in the nuclei and/or cytoplasm of the gland cells in an endometrial tissue sample from on or before day 18 of an idealized 28 day menstrual cycle from the woman;
   b) detecting expression of progesterone receptor in gland cells in an endometrial tissue sample from on or before day 18 of an idealized 28 day menstrual cycle from the woman;
   c) detecting the expression of MAG in the gland cells in an endometrial tissue sample on or before day 18 of an idealized 28 day menstrual cycle from the woman;
wherein said two or more steps are performed on serial sections of the sample.

* * * * *